(12) United States Patent
Karpol et al.

(10) Patent No.: US 6,924,891 B2
(45) Date of Patent: *Aug. 2, 2005

(54) METHOD AND APPARATUS FOR ARTICLE INSPECTION INCLUDING SPECKLE REDUCTION

(75) Inventors: Avner Karpol, Ziona (IL); Silviu Reinhorn, Mevaseret Zion (IL); Emanuel Elysaf, Rehovot (IL); Shimon Yalov, Holon (IL); Boaz Kenan, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 10/836,022

(22) Filed: Apr. 29, 2004

(65) Prior Publication Data

US 2004/0201842 A1 Oct. 14, 2004

Related U.S. Application Data

(60) Continuation of application No. 10/436,920, filed on May 12, 2003, now Pat. No. 6,798,505, which is a division of application No. 10/044,454, filed on Jan. 11, 2002, now Pat. No. 6,587,194, which is a division of application No. 09/443,247, filed on Nov. 17, 1999, now Pat. No. 6,369,888.

(51) Int. Cl.[7] .............................................. G01N 21/00
(52) U.S. Cl. ................................. 356/237.5; 356/237.4
(58) Field of Search .......................... 356/237.1–237.5, 356/500, 517, 392–394; 250/491.1, 492.2, 550, 492.1; 382/31, 141, 149

(56) References Cited

U.S. PATENT DOCUMENTS 3,778,785 A * 12/1973 von Gutfeld ................ 365/113
4,070,116 A    1/1978 Frosch et al.
4,508,453 A    4/1985 Hara et al.
4,560,235 A   12/1985 Servaes et al.

(Continued)

FOREIGN PATENT DOCUMENTS

| EP | 0 867 772 A2 | 3/1998 |
| JP | 363282640 A | 11/1988 |
| JP | 05-190421 A | 7/1993 |
| JP | 8-154210 A | 6/1996 |
| JP | 8-292361 A | 11/1996 |
| JP | 11-014357 A | 1/1999 |
| WO | WO98/01858 | * 7/1997 |
| WO | WO 00/70332 A1 | 11/2000 |

OTHER PUBLICATIONS

Patent Abstracts of Japan for JP 60 230629, Application date: Apr. 28, 1984.

(Continued)

*Primary Examiner*—Gregory J. Toatley, Jr.
*Assistant Examiner*—Sang H. Nguyen
(74) *Attorney, Agent, or Firm*—Sughrue Mion PLLC

(57) ABSTRACT

A method and apparatus for reducing speckle during inspection of articles used in the manufacture of semiconductor devices, including wafers, masks, photomasks, and reticles. The coherence of a light beam output by a coherent light source, such as a pulsed laser, is reduced by disposing elements in a light path. Examples of such elements include optical fiber bundles; optical light guides; optical gratings; an integrating sphere; and an acousto-optic modulator. These various elements may be combined as desired, such that light beams output by the element combinations have optical path length differences that are greater than a coherence length of the light beam output by the coherent light source.

22 Claims, 9 Drawing Sheets

U.S. PATENT DOCUMENTS

| | | |
|---|---|---|
| 4,627,731 A | 12/1986 | Waters et al. |
| 4,681,427 A | 7/1987 | Plummer |
| 4,734,923 A | 3/1988 | Frankel et al. |
| 4,760,265 A | 7/1988 | Yoshida et al. |
| 4,805,123 A | 2/1989 | Specht |
| 4,806,774 A * | 2/1989 | Lin et al. ............... 250/550 |
| 4,819,033 A | 4/1989 | Yoshitake et al. |
| 4,926,489 A | 5/1990 | Danielson |
| 4,997,259 A | 3/1991 | Ichimura et al. |
| 5,016,149 A | 5/1991 | Tanaka et al. |
| 5,159,455 A | 10/1992 | Cox et al. |
| 5,264,912 A | 11/1993 | Vaught et al. |
| 5,355,219 A | 10/1994 | Araki et al. |
| 5,355,425 A | 10/1994 | Braiman et al. |
| 5,463,497 A | 10/1995 | Muraki et al. |
| 5,471,066 A * | 11/1995 | Hagiwara ............ 250/559.48 |
| 5,479,238 A | 12/1995 | Whitney |
| 5,555,087 A | 9/1996 | Miyagawa et al. |
| 5,563,702 A * | 10/1996 | Emery et al. ............... 356/73 |
| 5,619,429 A | 4/1997 | Aloni |
| 5,652,665 A | 7/1997 | Chen et al. |
| 5,661,556 A | 8/1997 | Schiff et al. |
| 5,671,050 A | 9/1997 | De Groot |
| 5,691,541 A * | 11/1997 | Ceglio et al. ............ 250/492.1 |
| 5,699,447 A | 12/1997 | Alumot |
| 5,703,691 A | 12/1997 | Klaras et al. |
| 5,757,474 A | 5/1998 | Sopori et al. |
| 5,784,098 A | 7/1998 | Shoji et al. |
| 5,825,482 A | 10/1998 | Nikoonahad |
| 5,838,709 A | 11/1998 | Owa |
| 5,838,843 A | 11/1998 | Aose et al. |
| 5,859,924 A | 1/1999 | Liu et al. |
| 5,862,285 A | 1/1999 | Danielian et al. |
| 5,864,394 A | 1/1999 | Jordan, III |
| 5,892,579 A * | 4/1999 | Elyasaf et al. ........... 356/239.8 |
| 5,929,994 A | 7/1999 | Lee et al. |
| 6,028,664 A | 2/2000 | Cheng et al. |
| 6,072,581 A | 6/2000 | Stephenson et al. |
| 6,104,945 A | 8/2000 | Modell et al. |
| 6,169,603 B1 * | 1/2001 | Takayama ................ 356/500 |
| 6,184,976 B1 * | 2/2001 | Park et al. .............. 356/237.4 |
| 6,238,063 B1 | 5/2001 | Tanitsu et al. |
| 6,369,888 B1 * | 4/2002 | Karpol et al. ........... 356/237.5 |
| 6,377,336 B1 | 4/2002 | Shiraishi et al. |
| 6,381,015 B1 | 4/2002 | Sonehara et al. |
| 6,466,315 B1 * | 10/2002 | Karpol et al. ........... 356/237.4 |
| 6,693,664 B2 | 2/2004 | Neumann |
| 2002/0067478 A1 | 6/2002 | Karpol et al. |

OTHER PUBLICATIONS

Patent Abstracts of Japan for JP 60 247643, Application date: May 24, 1984.

T. S. McKechnie, *Speckle Reduction, in* Topics in Applied Physics, Laser Speckle and Related Phenomena, 123 (J.C. Dainty ed., 2d ed., 1984), pp. 123–170.

B. Dingel et al., *Speckle reduction with virtual incoherent laser illumination using a modified fiber array*, Optik 94, at 132 (1993), pp. 132–136.

* cited by examiner

METHOD AND APPARATUS FOR ARTICLE INSPECTION INCLUDING SPECKLE REDUCTION

This is a continuation of application Ser. No. 10/436,920 filed May 12, 2003; now U.S. Pat. No. 6,798,505, which is a divisional of application Ser. No. 10/044,454 filed Jan. 11, 2002 (now U.S. Pat. No. 6,587,194), which is a divisional of application Ser. No. 09/443,247 filed Nov. 17, 1999 (now U.S. Pat. No. 6,369,888); the disclosure of which is incorporated herein by reference.

BACKGROUND OF THE INVENTION

1. Field of the Invention

The present invention relates to inspection of articles, and in particular, to inspection of articles related to the manufacture of semiconductor devices. More specifically, the invention relates to the inspection of articles used in photolithography during the manufacture of semiconductor devices.

2. Description of the Related Art

Current demands for high density and performance associated with ultra large scale integration in semiconductor devices require submicron features, increased transistor and circuit speeds, and improved reliability. Such demands require formation of device features with high precision and uniformity, which in turn necessitates careful process monitoring.

One important process requiring careful inspection is photolithography, wherein masks or "reticles" are used to transfer circuitry patterns to semiconductor wafers. Typically, the reticles are in the form of patterned chrome over a transparent substrate. A series of such reticles are employed to project the patterns onto the wafer in a preset sequence. Each photolithographic reticle includes an intricate set of geometric patterns corresponding to the circuit components to be integrated onto the wafer. The transfer of the reticle pattern onto the photoresist layer is performed conventionally by an optical exposure tool such as a scanner or a stepper, which directs light or other radiation through the reticle to expose the photoresist. The photoresist is thereafter developed to form a photoresist mask, and the underlying polysilicon insulators or metal layer is selectively etched in accordance with the mask to form features such as lines or gates.

From the above description, it should be appreciated that any defect on the reticle, such as extra or missing chrome, may transfer onto the fabricated wafer in a repeated manner. Thus, any defect on the reticle would drastically reduce the yield of the fabrication line. Therefore, it is of utmost importance to inspect the reticles and detect any defects thereupon. The inspection is generally performed by an optical system, using transmitted, reflected, or both types of illuminations. An example of such a system is the RT-8000™ series reticle inspection system available from Applied Materials of Santa Clara, Calif.

There are several different known algorithm methods for inspection of reticles. These methods include: "Die to Die" inspection, in which a die is compared to a purportedly identical die on the same reticle; or "Die to Database" inspection, in which data pertaining to a given die is compared to information in a database, which could be the one from which the reticle was generated. Another inspection method involves Die to golden dye which is a dye chosen as a reference for inspecting wafers. There also is a design rule based inspection, in which the dye has to fulfill some line width and spacing requirements, and feature shapes should fit predefined shapes. Examples of these inspection methods, and relevant apparatus and circuitry for implementing these methods, are described in various U.S. patents, including, inter alia, U.S. Pat. Nos. 4,805,123; 4,926,489; 5,619,429; and 5,864,394. The disclosures of these patents are incorporated herein by reference.

Known inspection techniques typically use imaging the articles with a large magnification onto a charge-coupled device (CCD) camera. The imaging technique requires the article to be illuminated. The brightness of the illuminating source is a key factor in the ability to speed the inspection by reducing the integration time of the camera. As the patterns on wafers get smaller, it becomes necessary to use smaller wavelengths in order to be able to detect the patterns. This is due to the fact that the physical resolution limit depends linearly on the illumination wavelength and due to interference effects which require that the inspection be done at a wavelength similar to the one used in the lithographic process. As the wavelengths get smaller, conventional incoherent light sources like filament lamps or gas discharge lamps do not have enough brightness, and the light sources of choice become short wavelength lasers. The coherence of the laser, together with the roughness and aberrations of the surfaces as well as the patterned article along the light path, creates an artifact known as speckle, which is a noisy pattern over the image of the article.

Speckle causes problems in detection of the surfaces of articles being inspected and causes false alarms because of the non uniformity of the light pattern hitting the detector. Detection accuracy is degraded. Also, images taken of inspected articles are degraded. The problem is an acute one in this type of article inspection, because the power provided by coherent light is essential, among other reasons, as a result of losses stemming from the detection process.

The just-discussed problems are not unique to inspection of masks, photomasks, and reticles. There are known wafer inspection techniques which employ coherent illumination. In such systems, speckle can have an adverse impact on yield and performance of the resulting devices, and so also must be addressed with great care. Examples of known wafer inspection systems employing coherent illumination are shown in U.S. Pat. Nos. 5,699,447 and 5,825,482. The disclosures of these patents also are incorporated herein by reference.

When such systems are used to inspect patterned wafers, the speckle phenomenon can arise, if the spot size used for illumination is not much smaller than an element of a pattern on the wafer. However, in some circumstances, such as oblique illumination (in which the coherent light source is directed to the wafer at an angle), the spot size will be sufficiently large to cause speckle. Reducing the spot size will reduce system throughput and will require working at a wavelength that is smaller and different from the one used for imaging the article for example during the lithographic process. Consequently, as can be appreciated, there is a tradeoff between enduring speckle and optimizing detection sensitivity/throughput. Therefore, it would be desirable to solve the speckle problem, and thus enable the use of an increased spot size, and thus improve throughput.

A comprehensive description of speckle phenomena can be found in T. S. McKechnie, *Speckle Reduction*, in Topics in Applied Physics, Laser Speckle and Related Phenomena, 123 (J. C. Dainty ed., 2d ed., 1984) (hereinafter McKechnie). As discussed in the McKechnie article, speckle reduction may be achieved through reduction in the temporal coherence or the spatial coherence of the laser light. There have been various attempts over the years to reduce or eliminate speckle.

Another article, citing the above-mentioned McKechnie article and addressing the same issues, B. Dingel et al., *Speckle reduction with virtual incoherent laser illumination using a modified fiber array*, Optik 94, at 132 (1993) (hereinafter Dingel), mentions several known methods for reducing speckle based on a time integration basis, as well as based on statistical ensemble integration. With respect to the time integration methods, involving scanning of various planes of the imaging system and generating uncorrelated image patterns to be integrated by an image detector, the article identifies some possible drawbacks, such as a long integration time, or introduction of additional optical systems to support the scanning process.

Among the methods involving a reduction in the coherence of the beam, both Dingel and McKechnie discuss the introduction of a dispersing element, such as a grating, a screen mesh, or a moving diffuser, by itself or in combination with another rotating diffuser, into the path of the illuminating beam so as to produce a random phase modulation over the extent of the light beam. Other known techniques involve the passage of a pulsed laser beam through a carbon disulfide cell and further through an unaligned fiber optic bundle, or the use of liquid crystals interposed in the path of the light beam, the crystals being moved by electric field excitation.

However, as the reticles become smaller in size and the patterns shrink, it becomes more difficult to manufacture them with no fine anomalies and small defects. With diffraction effects, the detection becomes more complicated as well. Therefore, the danger exists that small defects may go undetected, which could cause problems in the related wafer manufacturing process. One proposed solution to the current situation involves the use of a laser light source emitting low wavelength laser beams, preferably in the deep ultraviolet (UV) region to illuminate the article. The laser source would preferably emit short pulses of light, with a preferred range of 5–50 nanoseconds. None of the methods and systems discussed above is equipped to offer a high level of speckle reduction for low wavelength laser beams so as to ensure accurate defect detection. Also, the above methods and systems do not provide a reliable solution for short laser pulses because of inadequate moving speed of the dispersing elements.

As alluded to previously, speckle also is a known phenomenon in the wafer inspection area. U.S. Pat. No. 5,264,912, the disclosure of which is incorporated herein by reference, identifies this problem, and provides some proposed solutions. However, as with other known and proposed speckle reduction techniques, these proposed solutions do not address particular problems resulting from the need to work with extremely small features, and the consequent need to employ coherent illumination sources with very low wavelengths.

Speckle reduction devices, interposed in the light path between the article surface and the detector, also can be expensive. For example, interposing a fiber bundle in accordance with one of the techniques described above could require as many as 10,000 fibers with different properties, such as length, in the bundle. These fiber bundles would be extremely large in size, and consequently would be expensive. It would be desirable to find a solution that did not need so many fibers.

A similar problem would pertain with respect to the use of a diffraction grating. The finer and larger in size the grating, the more expensive it would be. It would be desirable to find a solution, using diffraction gratings, but which did not require exceedingly fine gratings.

As can be appreciated from the foregoing discussion, there is a need in the art for a method and system for reducing speckle when inspecting articles using pulsed laser beams at low wavelengths, including the deep UV region.

SUMMARY OF THE INVENTION

In view of the foregoing, one feature of the invention is the provision of an optical system for reducing speckle during inspection of articles used in the manufacture of semiconductor devices.

Another feature of the present invention resides in the provision of an optical system for reducing speckle in inspection systems operating at low wavelengths, particularly in the deep UV region.

A further feature of the present invention is the reduction of speckle in inspection systems using pulsed laser beams, particularly using pulses in the 5–50 ns region.

To provide the foregoing and other features, to overcome the limitations in the prior art described above, and to solve various problems that will become apparent upon reading and understanding of the following detailed description, the present invention provides a method and apparatus for reducing speckle during the inspection of articles used in the fabrication of semiconductor devices, especially wafers, masks, photomasks, and reticles.

In accordance with the present invention, the inventive apparatus is constituted by a coherent light source, such as a laser, which outputs a coherent light beam along a light path. In one embodiment of the invention, two optical fiber bundles are disposed sequentially along the light path, each bundle having a predetermined number of fibers of different lengths, which may be arranged within the bundle. A first bundle receives the light beam and outputs several intermediate beams, one beam for each fiber of the bundle, each intermediate beam being imaged into all of the fibers of a second fiber bundle. Each of the fibers in the second bundle outputs an output beam, which then is used to illuminate the area under inspection of the article. Various optical devices for homogenizing the beam and focusing the beam, as are well known in the art, may be interposed at appropriate locations along the optical path.

As a variation on the preceding embodiment, the refractive indices of the fibers within the bundle may be varied. Using varying refractive indices may change the optical paths sufficiently to avoid the need to vary the lengths of the fibers as greatly.

As a further variation on the preceding embodiment, the fibers in the bundle may have the same or varying nonlinear characteristics. One attribute of employing varying nonlinearity is that the lengths of the fibers may not have to be varied as much. Having fibers of a consistent length may be advantageous from the standpoint of implementation.

In accordance with a further embodiment, the apparatus may be using one or more gratings disposed sequentially along the light path. The gratings operate similarly to the fibers, as discussed above.

In accordance with further embodiments of the invention, the apparatus may be constituted by more than two fiber bundles; more than two gratings; a fiber bundle and a grating, in either order; or some further combination of fiber bundle(s) and grating(s), in any desired sequence.

An advantage of each of the foregoing embodiments is that the individual elements are either simpler or smaller, and hence less expensive, than having a smaller number of larger, or more complex elements. For example, using two fiber bundles with 100 fibers in each bundle, with each fiber in the first bundle along the path providing an output to each fiber in the second bundle, will yield 100×100=10,000 different variants, just as if a single bundle with 10,000 different fibers were used.

A similar advantage applies with respect to the use of both gratings which are very good for introducing small optical path length variations, with fibers or light guides, which are convenient in introducing large optical path length variations.

In accordance with a further embodiment of the invention, an integrating sphere, having a first, input aperture and a second, output aperture, is disposed along the light path, the first aperture receiving the light beam and with the second aperture outputting a light beam, formed after the light beam has its path changed by being reflected within the integrating sphere. The integrating sphere may be constituted by two such spheres, with one being disposed concentrically within the other. The inner sphere would provide further reflection of the light within the integrating sphere.

The just-described embodiment is simpler, in some sense, than the previously described embodiments, but has certain disadvantages with respect to efficiency, based on currently available reflective materials. This is particularly so with the two-sphere embodiment. As these materials improve, it is expected that the integrating sphere approach will become an increasingly attractive alternative.

Yet another embodiment of the present invention is constituted by an electro or acousto-optic modulator disposed along the light path and having an input surface for receiving the light beam and an output surface for transmitting an incoherent modulated beam to the area to be inspected. The high frequency bandwidth at which the modulator operates will alter randomly the optical wavefront phase of the input beam sufficiently to reduce or eliminate speckle. This embodiment has something of a disadvantage as compared with the previous embodiments because, for the shorter wavelengths such as deep UV, -optical modulators are relatively expensive. Since this solution works very well for sources with long coherence lengths, it may be used in combination with a fiber bundle or a grating, which work well at reducing speckle from sources with small and medium coherence lengths.

BRIEF DESCRIPTION OF THE DRAWINGS

The above features and advantages of the present invention will become more apparent when referring to the following detailed description of preferred embodiments thereof with reference to the attached drawings in which like reference numbers represent corresponding parts throughout, in which.

DETAILED DESCRIPTION OF PREFERRED EMBODIMENTS

In the following description of preferred embodiments of the present invention, reference is made to the accompanying drawings, which form a part thereof, and which show by way of illustration specific embodiments of the invention. It is to be understood by those of working skill in this technological field that other embodiments may be utilized, and structural changes may be made without departing from the scope of the present invention.

Figure 1A:
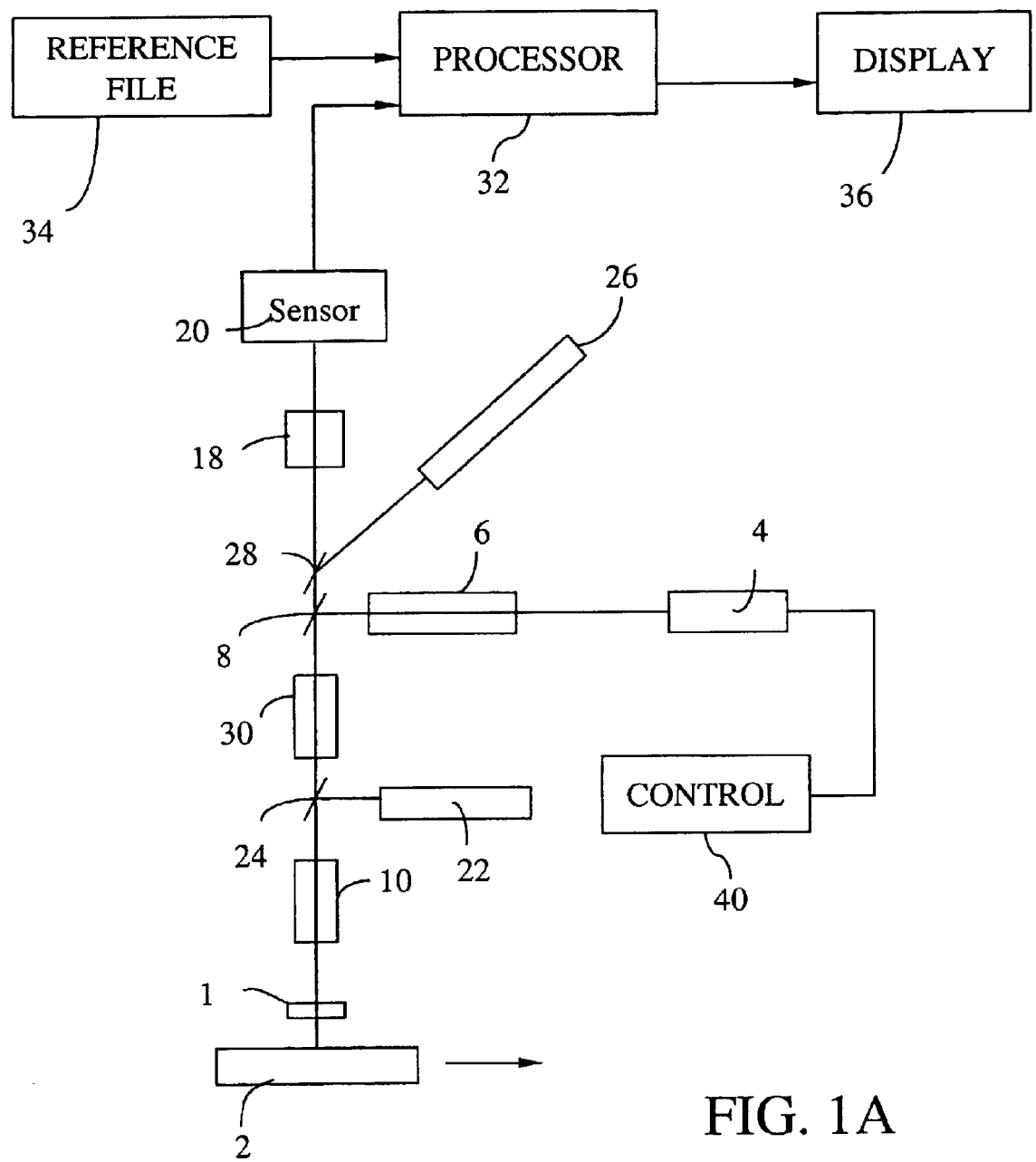
FIGS. 1A and 1B show examples of inspection devices for use in accordance with the present invention.

FIG. 1A shows an exemplary inspection device for use in accordance with the present invention. The inspection device shown in FIG. 1A is operating in a reflective mode. However, it is to be understood that inspection devices operating in a transmissive mode, or in both a transmissive and a reflective mode, are within the contemplation of the invention. At least for the transmissive mode of operation, a beam homogenizer should be employed prior to the beam's entering a coherence reduction/speckle reduction apparatus.

In FIG. 1A, an article 1 to be inspected, such as a wafer, a mask, a photomask, or a reticle, is positioned on an x-y stage 2, which moves the article 1 in two directions. The inspection device includes a coherent light source 4, preferably a laser, located on one side of the article 1. The light source 4 may be a continuous wave laser, or may be a pulsed laser, emitting low wavelength laser beams in the UV or deep UV region. The beams emitted by the light source 4 are directed via an optical system 6, a beam splitter 8 and an objective lens 10 onto the surface of the article 1. It should be noted that other means of directing the beams onto the article 1, including other optical paths defined by suitable structure, also may be used.

The light beams hitting the surface of article 1 are reflected via a relay lens 18 to an imaging detector 20. The imaging detector 20 may be a CCD sensor, which could be a 1×M sensor, or an N×M area or time delay integration (TDI) or CCD sensor. The sensor 20 enables imaging of the article 1, while allowing the stage 2 carrying the article 1 to move continuously relative to the light source 4.

The inspection device shown in FIG. 1 further includes a coherence reduction optical apparatus 30, positioned along the path of the light beam. The coherence reduction optical apparatus 30, in its various embodiments as discussed to some extent above, is a central focus of the invention. The inspection device also includes an autofocus device 22, controlling an objective lens 10 via a beam splitter 24, the objective lens 10 being also positioned along the path of the light beam, and a viewing eyepiece 26 receiving the reflected light beam via a beam splitter 28 for viewing purposes.

The light source 4 is controlled by a control system 40, which energizes the light source 4 to emit the light beams.

In operation, the light beam emitted by the light source 4 through the optical system hits the beam splitter 8 being directed towards the article 1. The effect of this illumination arrangement is generally to deliver normal illumination to the article 1. The light beam travels along a light path, being reflected through the coherence reduction optical apparatus 30, the beam splitter 24, and the objective lens 10, onto the article 1. Then, the light beam is reflected from the article 1, being imaged onto the sensor 20 via the relay lens 18.

The reflected light beam contains information about the pattern contained on the article 1, and also provides information regarding any defects present in the article 1 and on its surface. The coherent nature of the light source 4, and its wavelength of operation in comparison with the size of possible defects, can produce speckle at the sensor 20. Speckle causes unpredicted signal non uniformities, thus making it harder to distinguish the defects, and may allow some microscopic defects to remain undetected. Therefore, there is a need to reduce the speckle phenomenon by breaking the coherence of the light beam. The coherence reduction optical apparatus 30, positioned along the path of the light beam, reducing the coherence of the beam that hits the surface of the article 1, thereby reducing or eliminating speckle.

Figure 1B:
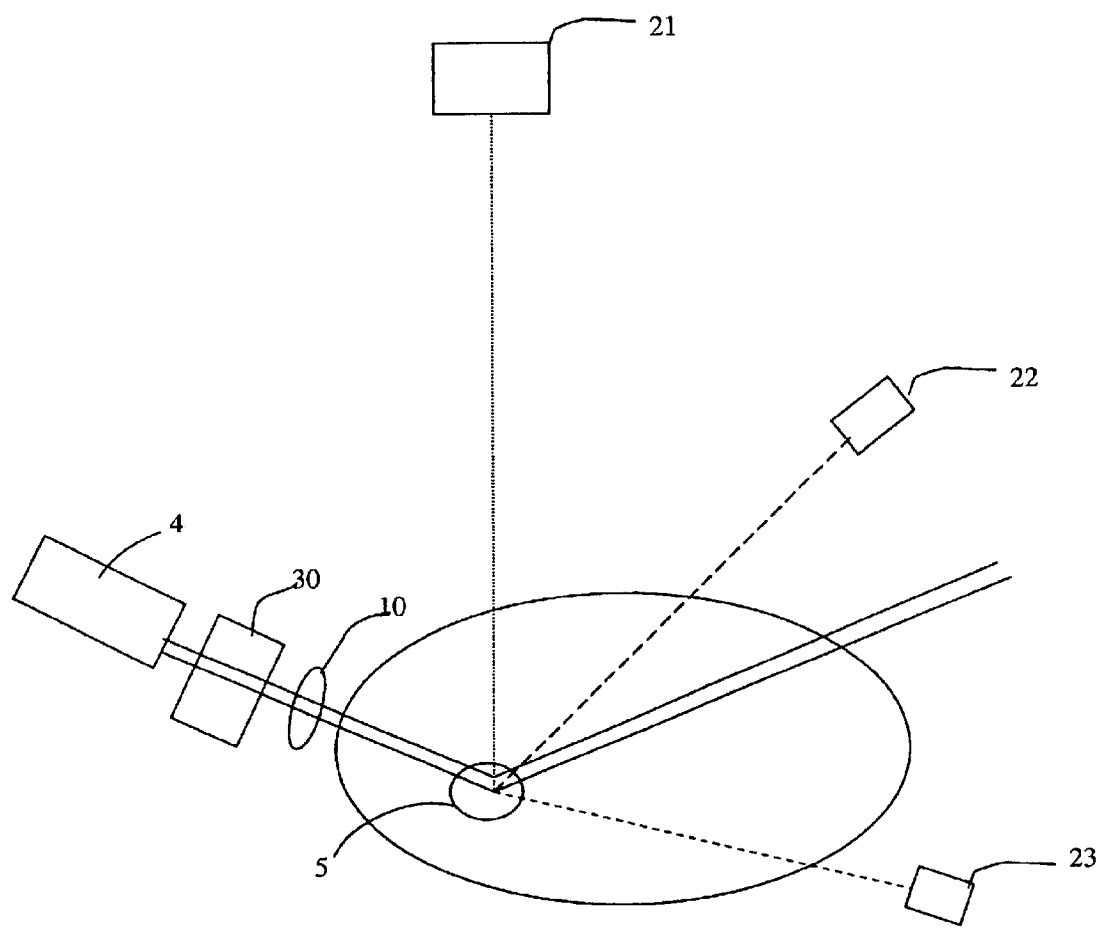

Another embodiment of an exemplary apparatus is shown in FIG. 1B, relating to wafer inspection systems employing oblique laser illumination. As shown, laser source 4 provides a laser beam that illuminates wafer 1 at an oblique angle, sometimes referred to as a grazing angle. As a result of the oblique angle, the illumination spot 5 has an oval shape, with a major axis of the oval elongated in the direction of illumination. This spot shape provides a relative large spot area, resulting in speckle.

In these types of systems, the detection scheme is based on dark field illumination. That is, the light beam is focused to a spot 5 using an objective 10. Since the wafer has a mirror-like surface, the light reflects according to Snell's law, as exemplified in the Figure. The dark field detectors are placed away from the beam reflection. Some examples of detector placement are shown as detectors 21, 22, and 23. Any combination of some or all of these detectors can be used. However, it should be appreciated that the speckle phenomenon can affect any or all of these detectors. Consequently, it is necessary to place the coherence reduction optical apparatus 30 in the illumination path of the laser beam.

Several embodiments of the coherence reduction optical apparatus 30 are provided in accordance with the present invention. Each embodiment now will be described in detail.

Figure 2A:
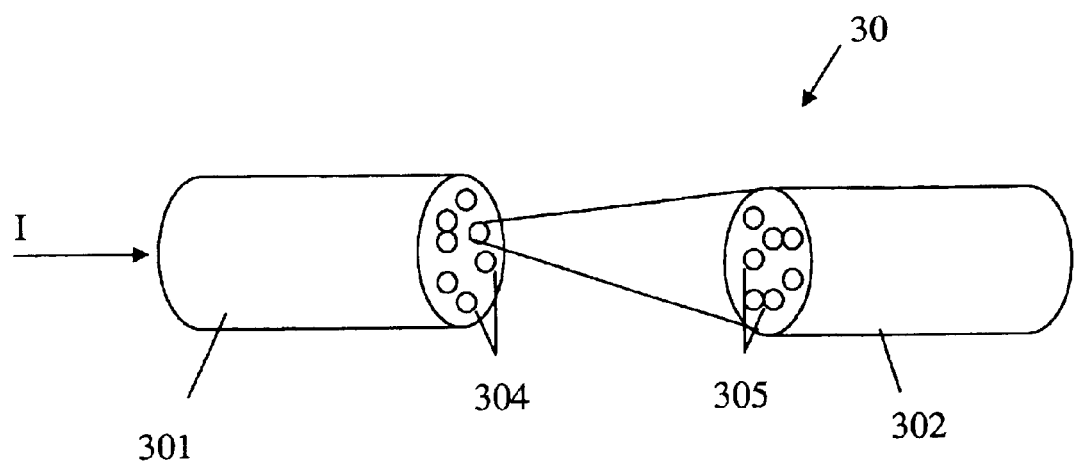
FIGS. 2A and 2B show a first embodiment of the present invention, and a variant thereof.

According to FIG. 2A, a first embodiment of the coherence reduction optical apparatus 30 includes two optical fiber bundles 301 and 302, each having a predetermined number of optical fibers 304, 305. The bundles may have the same number of fibers, or different numbers of fibers. There also may be more than two bundles provided. The optical bundles 301 and 302 are sequentially positioned along the path of the imaging beam I, bundle 301 being positioned ahead of bundle 302 and having an input for receiving the imaging beam I and an output adjacent to an input of the second bundle 302. (For ease of description, the two bundles 301, 302 are shown at a slight angle with respect to each other, though in operation they may be aligned along an axis.)

The optical fibers 304 and 305 are of a similar type known in the art, preferably having predetermined parameters, such as refractive index and cladding, although they could also have different refractive indices or different claddings. The fibers 304 and 305 have different lengths and may be randomly disposed within each bundle, using any of a number of known randomization techniques. The difference in length ΔL between any two fibers 304 is preferably selected to be greater than the coherence length of the light source 4. The difference in length between any pair 304 is preferably larger than the difference in length between the shortest and longest fiber in bundle 302. This will maximize the effect of the combined bundle, provided the right coupling is used. A general relationship among the fibers in the bundle is depicted in FIG. 3.

Figure 3:
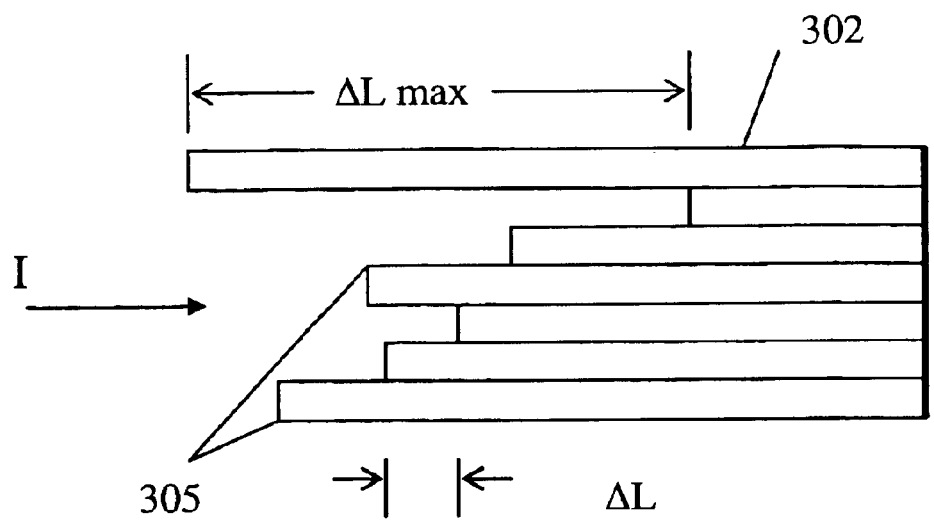
FIG. 3 is an explanatory diagram related to the first embodiment.

As also depicted in FIG. 3, one arrangement of the fibers 304 within the bundle 301 permits all of the ends of the fibers 304 at the output of the bundle 301 to be situated in a plane substantially transverse to the path of the imaging beam. Similarly, all ends of optical fibers 305 at the output end of bundle 302 may be situated in a plane substantially transverse to the path of the imaging beam. Another possibility is to use a bundle of closely packed light guides with varying lengths as shown in FIG. 3.

An example is the case of optical coherence length of 1 mm. For example, using a bundle of 25 fibers with lengths from 400 mm in increments of 20 mm, and a second bundle which consists of 36 closely packed square light guides with lengths of 20 mm in increments of 1 mm, the effect is as if a bundle of 25×36=900 fibers with length increments of 1 mm were used.

Figure 4:
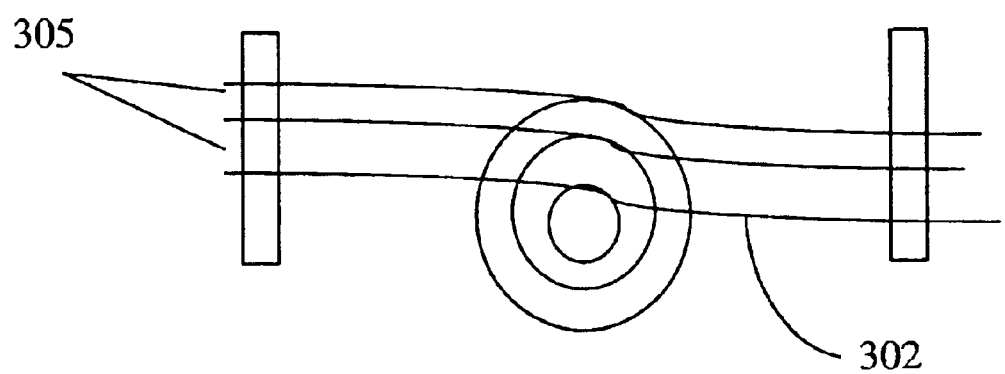
FIG. 4 shows a variant on the first embodiment.

The inputs of bundles 301 and 302 also may be situated in a plane transverse to the path of the imaging beam. In that event, since all of the fibers in each bundle have different lengths, some accommodation must be made for the difference in lengths, as for example by looping or bending some of the fibers in each bundle. Examples of arrangements of the fibers 304, 305 within the bundles 301, 302 are shown in FIG. 4. Those skilled in the art will recognize that fiber bundles having fibers of the same length, but with different refractive indices or different claddings could be used in lieu of the above preferred arrangements, with similar results.

Another variant on the optical fiber or light guiding bundle embodiment is that some or all of the fibers in each bundle may have nonlinear optical characteristics. Like the variation in refractive index or cladding, or variation in length of the fibers, the varying of nonlinear optical characteristics serves to vary the path length of the light passing through the fibers, and thus serves to reduce the coherence of the beam that is input onto article 1.

The nonlinear characteristics may be provided by using germanium doped glass, for example. Nonlinear characteristics also may be provided in a single light guide or glass rod. The nonlinear material produces self dual scattering at high power densities, thus enabling spectral broadening to a few hundred GHz, which in turn reduces coherence length, and thus reduces speckle.

When the wavefront of the imaging beam I hits the input of the first bundle 301, it is effectively broken into multiple optical beams, each beam penetrating one fiber 304 within the bundle 301 and travelling through the entire length of the fiber 304. At the output of the bundle 301, the beam coming out of each fiber 304 is imaged into preferably all fibers 305 of the bundle 302. Therefore, each fiber 305 receives light from all fibers 304. After the fibers 305 transmit the light through the output of the bundle 302, the resulting beams have optical path length differences which all are greater than the coherence length of the light source 4.

One advantage of imaging all of the light from each fiber 304 in bundle 301 into all of the fibers 305 in bundle 302, along with the length differences among the fibers in the bundles described above, is that the effect on reduction in coherence will be multiplicative, not additive. That is, for N fibers in bundle 301 and M fibers in bundle 305, the effect on coherence reduction will be as if N×M fibers were used, not N+M. As a result, for example, for N=M=100, the effect achieved with this technique is as if N×M=10,000 fibers were used, rather than 200. With this approach, it is possible to use far fewer fibers, and have a much less expensive coherence reduction structure. Other arrangements of lengths of fibers are possible, in which the effective number of outbound optical path lengths will be the product of the number of fibers in the bundles used, rather than their sum.

Figure 2B:
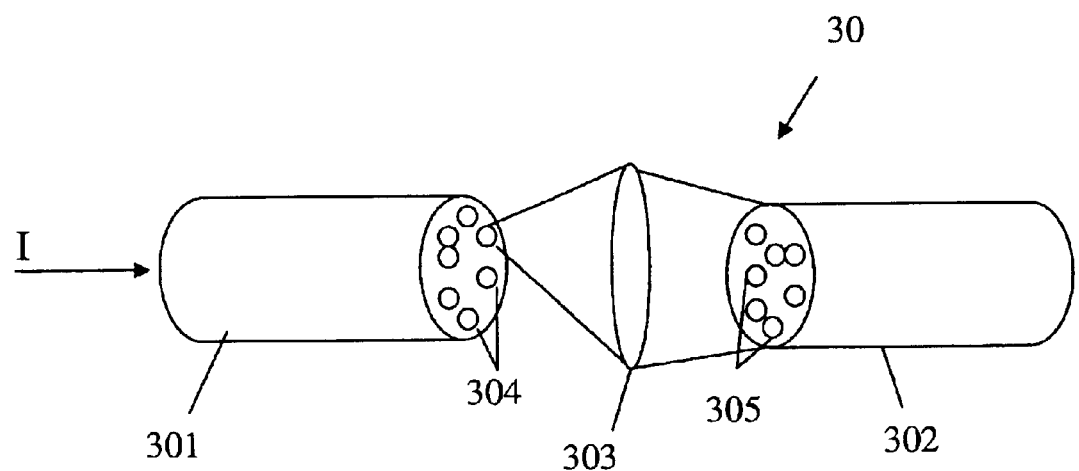

An advantage of using multiple fibers, rather than light guides or glass rods, is that the effective length of the coherence reduction optical apparatus can be very large. For example, by using 100 fibers in a bundle, having an increment of length of 50 mm, an effective length of 50 m can be achieved, packed into a box of only 0.5 m. As a result of application of the foregoing technique, coherence of the beam incident onto article 1 will be reduced, thereby reducing or eliminating speckle at the detector. In a variant on the first embodiment, as shown in FIG. 2B, the coherence reduction optical apparatus 30 may include an imaging lens 303 disposed in between the two bundles 301, 302 for imaging the beam coming out of each fiber 304 into all fibers 305 of the bundle 302. Those skilled in the art will appreciate that alternate embodiments of the present invention could include a plurality of optical fiber bundles, disposed sequentially along the path of the imaging beam I, and a plurality of imaging lenses 303 or other suitable optics interspersed among the bundles. A light scattering element may be introduced between the bundles to homogenize the angles at which the light hits the entrance of the next bundle.

Figure 5:
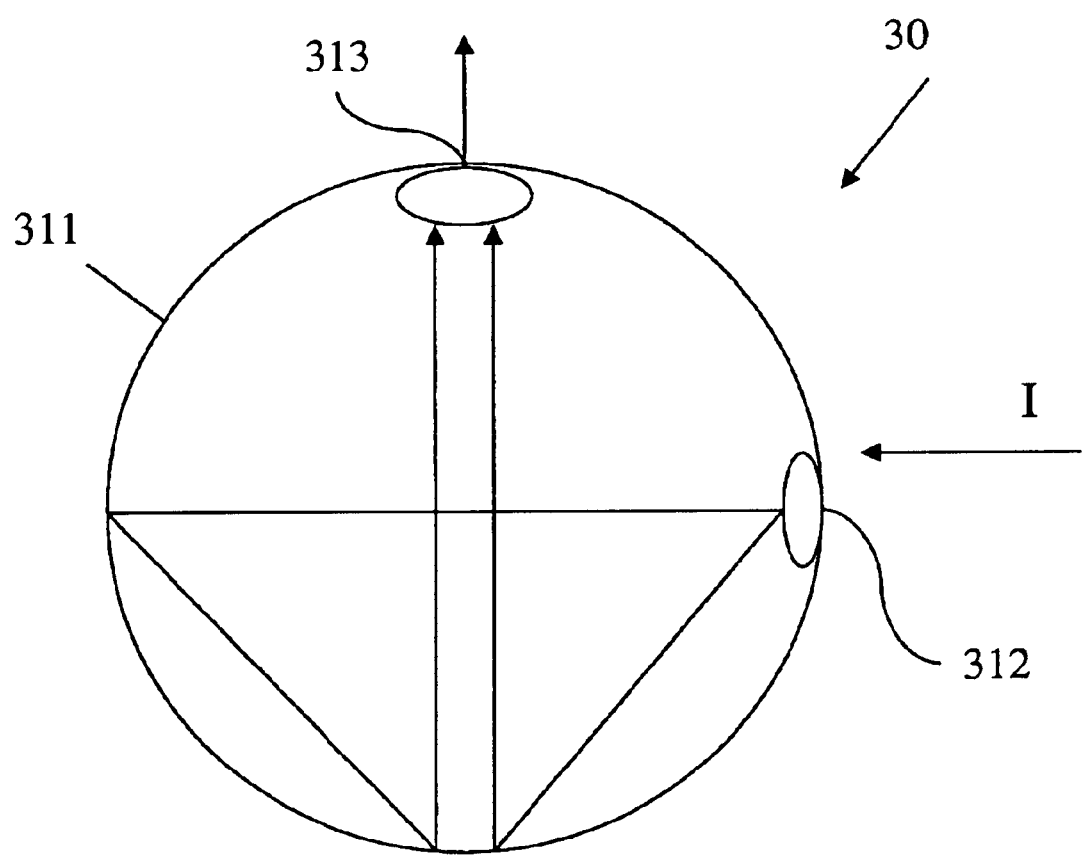
FIG. 5 shows a second embodiment of the present invention.

In a second embodiment of the present invention shown in FIG. 5, the coherence reduction optical apparatus 30 is constituted by an integrating sphere 311 disposed along the path of the imaging beam I. The integrating sphere 311 includes an entrance aperture 312 and an exit aperture 313. The aperture 312 has preferably a smaller diameter than the aperture 313. The aperture 312 is positioned so as to receive the imaging beam I. The integrating sphere 311 includes a non-absorbing inner surface made out of a non-absorbing material, preferably magnesium oxide (MgO), for better reflecting the imaging beam I. Other suitable reflective coatings also may be used.

After the imaging beam I is reflected within the integrating sphere 311, a reflected beam exits the sphere through the aperture 313. More specifically, the beam exiting the aperture 313 is a collection of reflected beams inside the integration sphere, each beam travelling a different distance from other beams. As a result, the collection of these beams exiting the aperture 313 is of reduced coherence as compared with the original imaging beam I.

Figure 6:
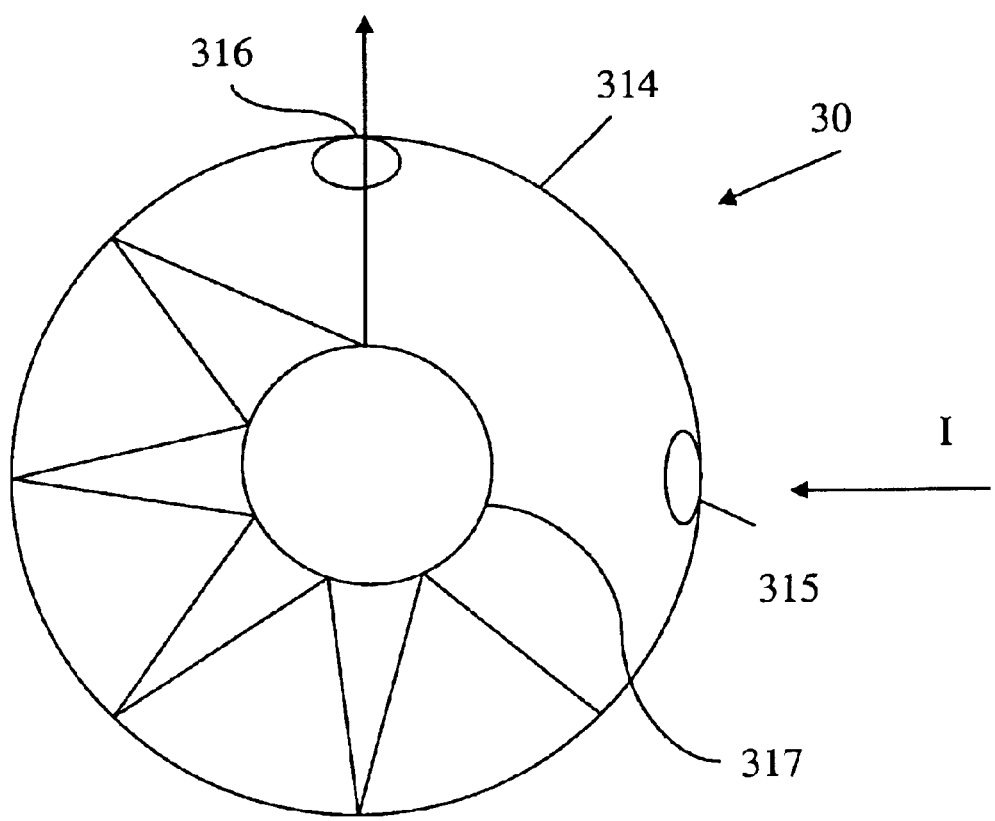
FIG. 6 shows a variant on the second embodiment.

In a variation on the just-described embodiment, as shown in FIG. 6, a second, inner sphere 317 is provided, having an outer surface which may be provided with the same non-absorbing material as the inner surface of the sphere 311. The inner sphere 317 and the integrating sphere 311 may be concentric, but this is not required. The imaging beam I entering the integrating sphere 311 through the aperture 312 is broken up into a collection of beams that are reflected by the inner sphere 317 and the inner surface of the integrating sphere 311. The resulting reflected beam which is transmitted to the article 1 through the aperture 313 is a collection of the reflected beams, and has reduced coherence. The effect of providing the inner sphere is to lengthen the reflective path of the light as it goes from entrance aperture 312 to exit aperture 313.

Various radii of the sphere 311, and diameters of the entrance and exit apertures are possible. Presently a radius of 25 mm for the sphere 311, a 1 mm entrance aperture, and a 5 mm exit aperture are preferred.

The embodiments of FIGS. 5 and 6 presently are considered to be less efficient than the optical fiber embodiment, because of losses attendant to use of the reflective material. The degradation resulting from the FIG. 6 embodiment in particular is considered quite disadvantageous. Providing a buffer of some kind before the entrance to the single-sphere embodiment of FIG. 5 may work better. It is expected that, as reflectivity of possible coatings improves, these embodiments will become more attractive.

Figure 7:
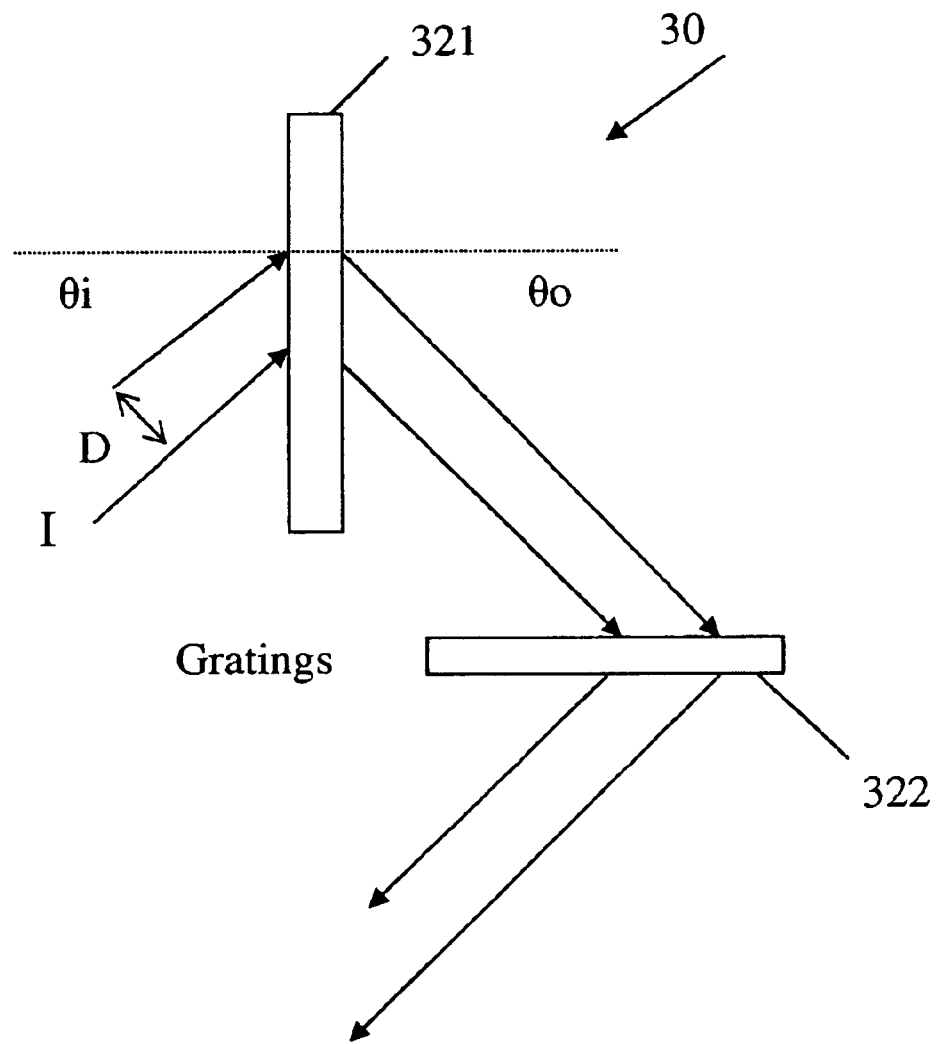
FIG. 7 shows a third embodiment of the present invention.

As shown in FIG. 7, a third embodiment of the coherence reduction optical apparatus 30 of present invention is constituted by a first grating 321 and a second grating 322, positioned along the path of the imaging beam I. The gratings 321, 322 in the embodiment are diffraction gratings, but it is to be understood that reflection gratings could be used with the same results. The gratings 321, 322 are preferably identical, having predetermined pitch $\Lambda$, wavelength $\lambda$, and first diffraction order, although gratings with different pitches and other properties could be used as well.

In operation, the imaging beam I hits the surface of grating 321 at a predetermined angle $\theta_i$, and is diffracted at an angle $\theta_o$. If the imaging beam I could be expanded to have a diameter D, as seen in FIG. 7, then an optical path difference (OPD) achieved between the two edges of the imaging beam can be calculated with the formula: OPD=D tan $\theta_i$+D sin $\theta_o$/cos $\theta_i$. The diffraction relation is sin $\theta_o$=$\lambda$/$\Lambda$−cos $\theta_i$. The diffracted light beam subsequently hits the second grating 322 and is diffracted. The angle of incidence can be the same angle, $\theta_i$, as before, and the outgoing angle, $\theta_o$, also can be the same as before. Applying the same calculations, the optical path difference of the resulting beam is 2·OPD. It can be seen from the above calculations that the optical path difference between the light source and the article can be broadened by disposing several similar gratings along the path of the beam I. It is arranged to deflect the light in the same rotational direction, for example clockwise, until $OPD_n$=n·OPD is greater than the coherence length of the light source. At that moment, the resulting beam will be incoherent and the process will reduce the speckle phenomenon. The calculations presented above could also be applied if reflection gratings are being used in an alternate embodiment instead of the diffraction gratings.

It should be noted that, as a result of the use of gratings in the embodiment of FIG. 7, the path of imaging beam I changes. The arrangement can be such that the entrance and exit beams have the same cross section, even though in between the gratings, the effective cross section in the meaningful direction will be much larger. The design is such that the final grating surface is perpendicular to the direction of propagation of the light. This enables, for example, the use of an illumination scheme from that point to the article, called Kohler illumination. Depending on the number of gratings provided, suitable optics would have to be provided to direct the coherence-reduced beam suitably onto article 1. Alternatively, the light source 10 could be positioned appropriately with respect to coherence reduction optical apparatus 30 so that the beam output from apparatus 30 would be directed properly onto article 1.

Instead of using multiple gratings, light can be passed multiple times through the same grating, using appropriate mirrors or other reflection/deflection units to redirect the light, for example, along a path similar to that shown in FIG. 7, i.e. redirection at 90° intervals. Redirection at other intervals also is acceptable.

Figure 8:
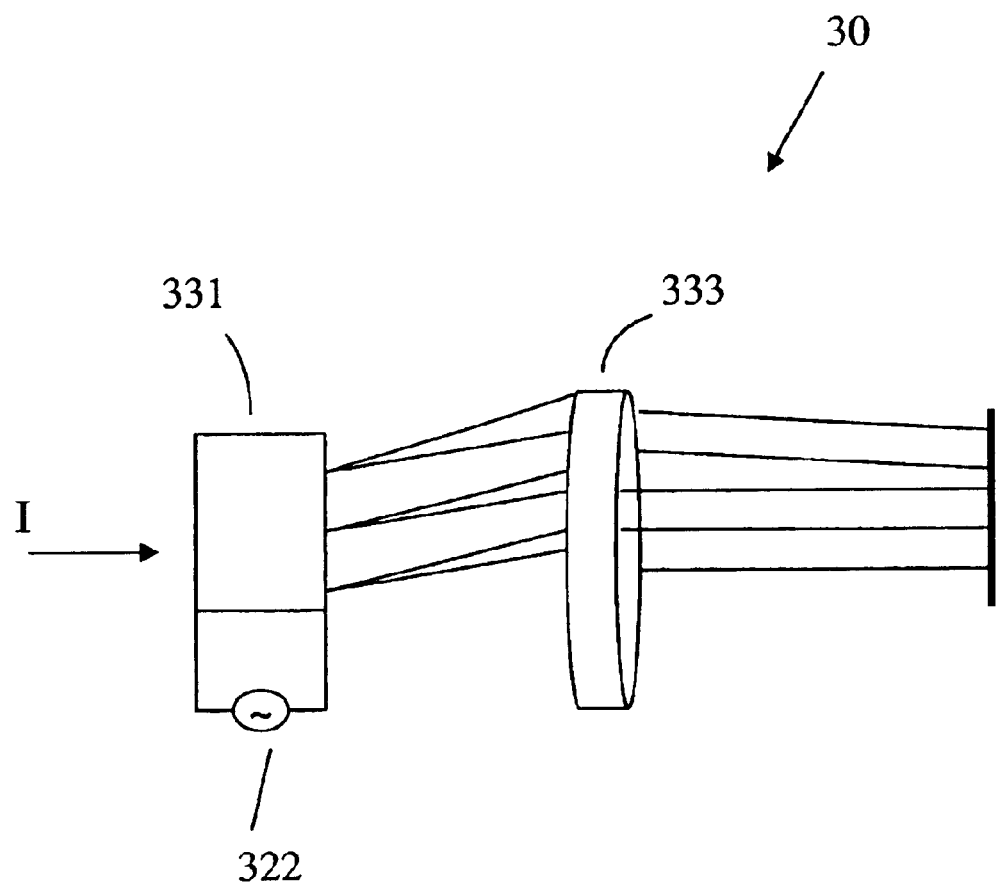
FIG. 8 shows a fourth embodiment of the present invention.

A fourth embodiment of the coherence reduction optical apparatus 30 is shown in FIG. 8. As seen in FIG. 8, the apparatus 30 is constituted by an acousto-optic modulator 331, positioned along the path of the imaging beam I, and ahead of an imaging lens 333. The acousto-optic modulator 331 is coupled to a source of electronic white noise 332 supplying a white noise signal with frequencies which may be in the 1–20 GHz range. The imaging beam I hits a relatively large surface of the modulator 331 at a predetermined angle, the surface having portions with different frequencies in the same 1–20 GHz range. The imaging beam I is then diffracted by these perturbations in the modulator and undergoes changes in direction and wavelength. Therefore, at the output of the modulator 331, the resulting modulated beam has non-coherent properties and can be imaged onto the article using the imaging lens 333. The optical arrangement may be similar to the one used in the system with the grating. Also, an acousto-optics modulator, or an electro-optic modulator maybe used with a grating, to account for both long and short coherence lengths.

One aspect of this embodiment is the ability to lengthen the duration of pulses received from a pulsed laser so that they exceed the coherence length of the imaging beam, and allow a more effective way of using a rotating diffuser. Assume the pulse length can be stretched from 5 ns to 50 ns by using a fiber bundle with fiber length differences up to 20 m. A rotating ground glass 100 mm in diameter, rotating at 30,000 RPM for example, may reduce the speckle modulation by a factor of 5.

Various combinations of the just-described embodiments also are possible. For example, a fiber bundle could be used with a diffraction grating, or with an acousto-optic modulator; a diffraction grating could be used with an acousto-optic modulator; and so on. The orders in which the various components of the coherence reduction optical apparatus 30 are placed are not necessarily critical; however, it is appropriate to reiterate the above caveat with respect to the relation of the element placed nearest the beam source, and coherence length, in order to secure the multiplicative advantage of the use of smaller fiber bundles discussed earlier.

Figure 9:
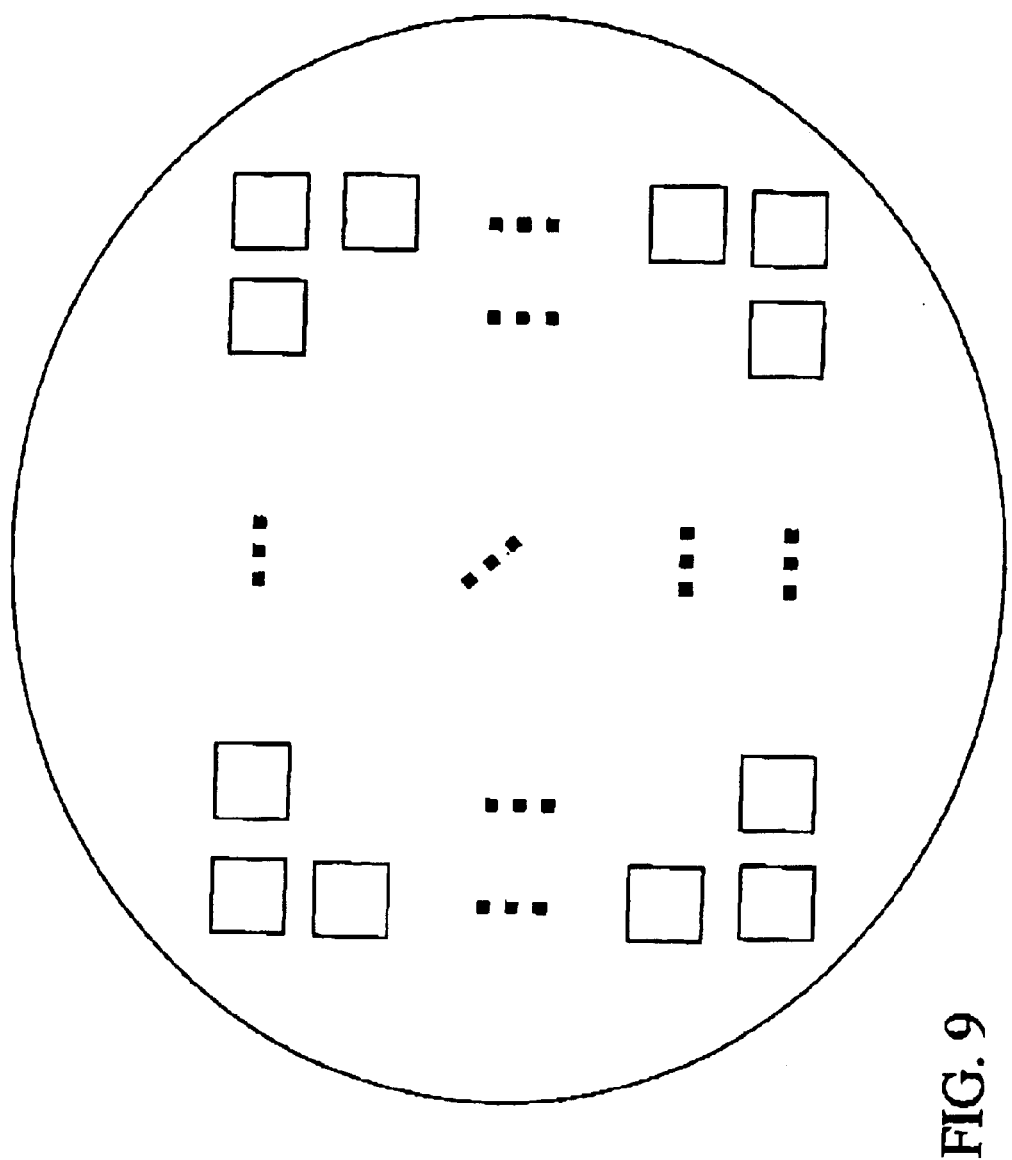
FIG. 9 shows an example of a wafer on which the method and apparatus of the present invention may be practiced.

While the invention has been described as set forth above with reference to several preferred embodiments, various embodiments within the scope and spirit of the invention will be apparent to those of working skill in this technological field. For example, while the preferred embodiment has been described in the context of a reticle used in semiconductor manufacture, it is within the contemplated scope of the invention to apply this simple, powerful technique to inspection of other patterned articles used in semiconductor manufacturing, or to semiconductor wafer inspection. Indeed, the inventive method and apparatus are applicable equally to inspection of wafers such as the one shown in FIG. 9, as well as to masks, photomasks, reticles, or any other such product used in similar fashion in the manufacture of semiconductor devices, as for example by a photolithographic process. Hence, so far as the inventive method and apparatus are concerned, the terms "mask," "photomask," and "reticle," and terms defining similar articles, are interchangeable, and should be so understood by those of working skill in this field.

Moreover, the coherence reduction techniques of the invention are not limited in applicability to inspection systems, but instead may be used in any semiconductor-related manufacturing operation where coherence reduction techniques are needed.

In view of the foregoing and other modifications which will be apparent to those of working skill in this field, the scope of the invention described herein should be considered to be limited only by the appended claims.

What is claimed is:

1. In the inspection of a patterned article used in the manufacture of semiconductor devices, a method of reducing speckle, said method comprising:
    effecting relative movement between an illuminating beam and said patterned article, said illuminating beam being obtained by modifying a coherent light beam so as to break, at least partially, its coherence;
    said modifying of said coherent light beam comprising:
    disposing a plurality of optical fiber bundles sequentially along a light path between a source of said illuminating beam and the patterned article, each of said plurality of fiber bundles having a predetermined number of fibers, each of said fibers having an input and an output, wherein fibers of a first bundle of said plurality of bundles receive said coherent light beam through said input and fibers of a last bundle of said plurality of bundles transmit an output beam through said output.

2. A method as claimed in claim 1, wherein said patterned article is selected from the group consisting of wafers, masks, photomasks, and reticles.

3. A method as claimed in claim 2, wherein there are first and second optical fiber bundles, said second optical fiber bundle being said last bundle, the method further comprising providing an output of each of the fibers in said first optical fiber bundle to an input of each of the fibers in said second optical fiber bundle.

4. A method as claimed in claim 3, wherein said predetermined number of fibers is different for each of said first and second optical fiber bundles.

5. A method as claimed in claim 3, wherein said predetermined number of fibers is the same for each of said first and second optical fiber bundles.

6. A method as claimed in claim 3, wherein at least some of the fibers in said first and second optical fiber bundles have different lengths.

7. A method as claimed in claim 6, wherein input ends of the fibers in at least one of said first and second optical fiber bundles are aligned.

8. A method as claimed in claim 6, wherein output ends of the fibers in at least one of said first and second optical fiber bundles are aligned.

9. A method as claimed in claim 3, wherein characteristics of at least some of the fibers in said first and second optical fiber bundles are selected from the group consisting of nonlinearity, difference in refractive indices, and difference in cladding.

10. An inspection device, comprising: a source of a coherent light beam; and an optical apparatus, the apparatus comprising a plurality of optical fiber bundles positioned sequentially along a light path between the source and a patterned article to be inspected so as to break, at least partly, a coherence of said coherent light beam, each of said plurality of fiber bundles comprising a predetermined number of fibers, each of said fibers having an input and an output, wherein fibers of a first bundle of said plurality of bundles receive said light beam through said input and fibers of a last bundle of said plurality of bundles transmit an output beam through said output.

11. A device as claimed in claim 10, wherein said patterned article is selected from the group consisting of wafers, masks, photomasks, and reticles.

12. A device as claimed in claim 11, wherein there are first and second optical fiber bundles, said second optical fiber bundle being said last bundle, wherein an output of each of the fibers in said first optical fiber bundle is provided to an input of each of the fibers in said second optical fiber bundle.

13. A device as claimed in claim 12, wherein said predetermined number of fibers is different for each of said first and second optical fiber bundles.

14. A device as claimed in claim 12, wherein said predetermined number of fibers is the same for each of said first and second optical fiber bundles.

15. A device as claimed in claim 12, wherein at least some of the fibers in said first and second optical fiber bundles have different lengths.

16. A device as claimed in claim 12, wherein input ends of the fibers in at least one of said first and second optical fiber bundles are aligned.

17. A device as claimed in claim 12, wherein output ends of the fibers in at least one of said first and second optical fiber bundles are aligned.

18. A device as claimed in claim 12, wherein characteristics of at least some of the fibers in said first and second optical fiber bundles are selected from the group consisting of nonlinearity, difference in refractive indices, and difference in cladding.

19. A method for electro-optically inspecting a patterned semiconductor wafer of dies for a defect, the method comprising:

providing a repetitively pulsed laser illuminating source which produces a coherent laser beam;

breaking at least partially a coherence of said coherent laser beam to produce an output light beam;

illuminating at least one field of view in each of a plurality of wafer dies using said output light beam; and detecting a wafer defect using a die-to-die comparison method, wherein the breaking at least partially a coherence of said coherent laser beam comprises disposing a plurality of optical fiber bundles sequentially along a light path between a source of said illuminating beam and the patterned semiconductor wafer, each of said plurality of fiber bundles having a predetermined number of fibers, each of said fibers having an input and an output, wherein fibers of a first bundle of said plurality of bundles receive said coherent light beam through said input and fibers of a last bundle of said plurality of bundles transmit an output beam through said output.

20. A system for electro-optically inspecting a patterned semiconductor wafer of dies for a defect comprising:

a repetitively pulsed laser illuminating source, providing a coherent laser beam for illuminating at least one field of view in each of a plurality of wafer dies;

optical apparatus for breaking at least partially a coherence of said coherent laser beam to produce an output light beam; and a wafer defect detector, detecting a wafer defect using a die-to-die comparison method, wherein the optical apparatus for breaking at least partially a coherence of said coherent laser beam comprises a plurality of optical fiber bundles positioned sequentially along a light path of the coherent laser beam between the repetitively pulsed laser illuminating source and the patterned semiconductor wafer, each of said plurality of fiber bundles comprising a predetermined number of fibers, each of said fibers having an input and an output, wherein fibers of a first bundle of said plurality of bundles receive said light beam through said input and fibers of a last bundle of said plurality of bundles transmit an output beam through said output.

21. An electro-optical device for inspecting a patterned semiconductor wafer containing dies for a defect comprising:

a repetitively pulsed laser illuminating source, providing a coherent laser beam for illuminating at least one field of view in each of a plurality of dies;

optical apparatus for breaking at least partially a coherence of said coherent laser beam to produce an output light beam; and an imaging assembly including at least one detector ensemble including at least one two-dimensional matrix photo-detector, wherein the optical apparatus of breaking at least partially a coherence of said coherent laser beam comprises: a plurality of optical fiber bundles positioned sequentially along a light path of the coherent laser beam between the repetitively pulsed laser illuminating source and the patterned semiconductor wafer, each of said plurality of fiber bundles comprising a predetermined number of fibers, each of said fibers having an input and an output, wherein fibers of a first bundle of said plurality of bundles receiving said light beam through said input and fibers of a last bundle of said plurality of bundles transmitting an output beam through said output.

22. A method for electro-optically inspecting a patterned semiconductor wafer containing dies for a defect, comprising:

providing an imaging assembly including at least one detector ensemble including at least one two-dimensional matrix photo-detector;

providing a repetitively pulsed laser illuminating source which produces a coherent laser beam; and breaking at least partially a coherence of said coherent laser beam to produce an output light beam, wherein the breaking at least partially a coherence of said coherent laser beam comprises disposing a plurality of optical fiber bundles sequentially along a light path between a source of said illuminating beam and the patterned semiconductor wafer, each of said plurality of fiber bundles having a predetermined number of fibers, each of said fibers having an input and an output, wherein fibers of a first bundle of said plurality of bundles receiving said coherent light beam through said input and fibers of a last bundle of said plurality of bundles transmitting an output beam through said output.

* * * * *

UNITED STATES PATENT AND TRADEMARK OFFICE
CERTIFICATE OF CORRECTION

| | | |
|---|---|---|
| PATENT NO. | : 6,924,891 C1 | Page 1 of 1 |
| APPLICATION NO. | : 90/008414 | |
| DATED | : May 10, 2011 | |
| INVENTOR(S) | : Avner Karpol et al. | |

It is certified that error appears in the above-identified patent and that said Letters Patent is hereby corrected as shown below:

Claim 20, Column 2, Line 26, before "using" insert -- defect --.

Claim 22, Column 2, Line 11, delete "reptitively" and insert -- repetitively -- therefor.

Claim 37, Column 4, Line 23, delete "imputs" and insert -- inputs -- therefor.

Claim 78, Column 6, Line 51, delete "beams." and insert -- beam. -- therefor.

Signed and Sealed this
Eighth Day of November, 2011

David J. Kappos
*Director of the United States Patent and Trademark Office*

(12) EX PARTE REEXAMINATION CERTIFICATE (8218th)
United States Patent
Karpol et al.

(10) Number: US 6,924,891 C1
(45) Certificate Issued: May 10, 2011

(54) METHOD AND APPARATUS FOR ARTICLE INSPECTION INCLUDING SPECKLE REDUCTION

(75) Inventors: Avner Karpol, Ziona (IL); Silviu Reinhorn, Mevaseret Zion (IL); Emanuel Elysaf, Rehovot (IL); Shimon Yalov, Holon (IL); Boaz Kenan, Rehovot (IL)

(73) Assignee: Applied Materials, Inc., Santa Clara, CA (US)

Reexamination Request:
No. 90/008,414, Jan. 4, 2007

Reexamination Certificate for:
Patent No.: 6,924,891
Issued: Aug. 2, 2005
Appl. No.: 10/836,022
Filed: Apr. 29, 2004

Related U.S. Application Data

(60) Continuation of application No. 10/436,920, filed on May 12, 2003, now Pat. No. 6,798,505, which is a division of application No. 10/044,454, filed on Jan. 11, 2002, now Pat. No. 6,587,194, which is a division of application No. 09/443,247, filed on Nov. 17, 1999, now Pat. No. 6,369,888.

(51) Int. Cl.
*G01N 21/00* (2006.01)

(52) U.S. Cl. .......................... 356/237.5; 356/237.4
(58) Field of Classification Search .......................... None
See application file for complete search history.

(56) References Cited

U.S. PATENT DOCUMENTS

| | | | |
|---|---|---|---|
| 3,790,280 A | 2/1974 | Heinz et al. | |
| 3,905,019 A | 9/1975 | Aoki et al. | |
| 4,155,630 A | 5/1979 | Ih | |
| 4,202,631 A | 5/1980 | Uchiyama et al. | |
| 4,360,372 A | 11/1982 | Maciejko | |
| 4,360,799 A | 11/1982 | Leighty et al. | |
| 4,377,340 A | 3/1983 | Green et al. | |
| 4,428,672 A | 1/1984 | Allard et al. | |
| 4,448,532 A | 5/1984 | Joseph et al. | |
| 4,478,481 A | 10/1984 | Fusek et al. | |

(Continued)

FOREIGN PATENT DOCUMENTS

| | | |
|---|---|---|
| EP | 0 017 371 | 3/1980 |
| EP | 0 294 643 | 5/1988 |
| EP | 0628806 | 12/1994 |
| JP | 08-094338 | 4/1996 |
| JP | H11-101925 | 4/1999 |
| WO | WO 91/07683 | 5/1991 |
| WO | WO 95/09358 | 4/1995 |
| WO | WO 98/25399 | 6/1998 |
| WO | WO-99/46835 | 9/1999 |
| WO | WO 00/68884 | 11/2000 |
| WO | WO 01/13098 | 2/2001 |

OTHER PUBLICATIONS

Born, Max, et al. (1980). *Principles of Optics*. Sixth Edition, pp. 524–526, Figure 10.14.

Dingel, B., et al. (1992). "Laser–diode microscope with fiber illumination," *Optics Communications*, vol. 93(3):27–32.

Dingel, B., et al. (1993). "Speckle Reduction with Virtual Incoherent Laser Illumination Using a Modified Fiber Array," *Optik*, vol. 93(3):132–136.

(Continued)

*Primary Examiner* — M. Steelman

(57) ABSTRACT

A method and apparatus for reducing speckle during inspection of articles used in the manufacture of semiconductor devices, including wafers, masks, photomasks, and reticles. The coherence of a light beam output by a coherent light source, such as a pulsed laser, is reduced by disposing elements in a light path. Examples of such elements include optical fiber bundles; optical light guides; optical gratings; an integrating sphere; and an acousto-optic modulator. These various elements may be combined as desired, such that light beams output by the element combinations have optical path length differences that are greater than a coherence length of the light beam output by the coherent light source.

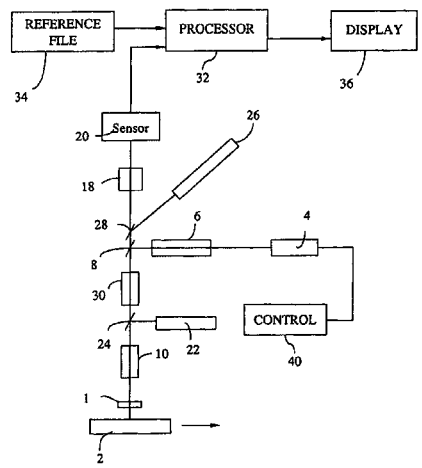

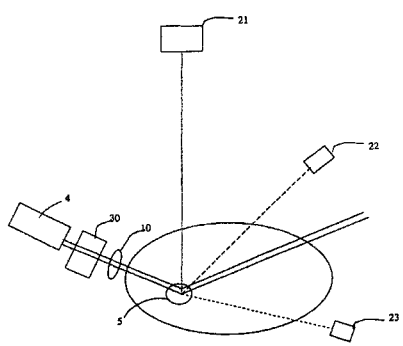

U.S. PATENT DOCUMENTS

| | | |
|---|---|---|
| 4,497,015 A | 1/1985 | Konno et al. |
| 4,513,384 A | 4/1985 | Rosencwaig |
| 4,521,075 A | 6/1985 | Obenschain et al. |
| 4,566,757 A | 1/1986 | Fusek et al. |
| 4,589,783 A | 5/1986 | Thomas et al. |
| 4,598,997 A | 7/1986 | Steigmeier et al. |
| 4,619,508 A | 10/1986 | Shibuya et al. |
| 4,628,531 A | 12/1986 | Okamoto et al. |
| 4,647,975 A | 3/1987 | Alston et al. |
| 4,659,172 A | 4/1987 | Cavan |
| 4,710,030 A | 12/1987 | Tauc et al. |
| 4,712,851 A | 12/1987 | Fusek et al. |
| 4,729,019 A | 3/1988 | Rouvrais |
| 4,772,126 A | 9/1988 | Allemand et al. |
| 4,860,371 A | 8/1989 | Matsuyama et al. |
| 4,874,251 A | 10/1989 | Thomas et al. |
| 4,882,498 A | 11/1989 | Cochran et al. |
| 4,896,211 A | 1/1990 | Hunt et al. |
| 4,909,615 A | 3/1990 | Ueda et al. |
| 4,910,690 A | 3/1990 | Fujita |
| 4,941,980 A | 7/1990 | Halavee et al. |
| 4,972,093 A | 11/1990 | Cochran et al. |
| 4,978,224 A | 12/1990 | Kishimoto et al. |
| 4,978,862 A | 12/1990 | Silva et al. |
| 4,991,968 A | 2/1991 | Yonescu et al. |
| 5,027,418 A | 6/1991 | Ikegaya et al. |
| 5,031,112 A | 7/1991 | Sakai et al. |
| 5,038,048 A | 8/1991 | Maeda et al. |
| 5,042,952 A | 8/1991 | Opsal et al. |
| 5,233,460 A | 8/1993 | Partlo et al. |
| 5,307,207 A | 4/1994 | Ichihara |
| 5,333,052 A | 7/1994 | Finarov |
| 5,381,004 A | 1/1995 | Uritsky et al. |
| 5,422,724 A | 6/1995 | Kinney et al. |
| 5,497,007 A | 3/1996 | Uritsky et al. |
| 5,546,811 A | 8/1996 | Rogers et al. |
| 5,633,711 A | 5/1997 | Nelson et al. |
| 5,689,351 A | 11/1997 | Hong |
| 5,715,345 A | 2/1998 | McKinley |
| 5,748,317 A | 5/1998 | Maris et al. |
| 5,748,318 A | 5/1998 | Maris et al. |
| 5,760,408 A | 6/1998 | Kikuchi et al. |
| 5,844,684 A | 12/1998 | Maris et al. |
| 5,854,674 A | 12/1998 | Lin |
| 5,892,579 A | 4/1999 | Elyasaf et al. |
| 5,985,680 A | 11/1999 | Singhal et al. |
| 6,011,643 A | 1/2000 | Wunderlich et al. |
| 6,057,927 A | 5/2000 | Levesque et al. |
| 6,078,386 A | 6/2000 | Tsai et al. |
| 6,081,330 A | 6/2000 | Nelson et al. |
| 6,103,539 A | 8/2000 | Schaffer et al. |
| 6,122,046 A | 9/2000 | Almogy |
| 6,141,038 A | 10/2000 | Young et al. |
| 6,172,349 B1 | 1/2001 | Katz et al. |
| 6,178,257 B1 | 1/2001 | Alumot et al. |
| 6,211,961 B1 | 4/2001 | Maris |
| 6,236,454 B1 | 5/2001 | Almogy |
| 6,248,988 B1 | 6/2001 | Krantz |
| 6,249,381 B1 | 6/2001 | Suganuma |
| 6,256,093 B1 | 7/2001 | Ravid et al. |
| 6,268,093 B1 | 7/2001 | Kenan et al. |
| 6,271,921 B1 | 8/2001 | Maris et al. |
| 6,285,855 B1 | 9/2001 | Tsuji |
| 6,317,514 B1 | 11/2001 | Reinhorn et al. |
| 6,321,601 B1 | 11/2001 | Maris |
| 6,366,352 B1 | 4/2002 | Goldberg et al. |
| 6,369,888 B1 | 4/2002 | Karpol et al. |
| 6,469,784 B2 | 10/2002 | Goldberg et al. |
| 6,587,193 B1 | 7/2003 | Reinhron et al. |
| 6,587,194 B2 | 7/2003 | Karpol et al. |
| 6,587,794 B1 | 7/2003 | Maznev |
| 6,590,698 B1 | 7/2003 | Ohtsuki et al. |
| 6,614,924 B1 | 9/2003 | Aghajan |
| 6,661,508 B2 | 12/2003 | Eytan et al. |
| 6,693,664 B2 | 2/2004 | Neumann |
| 2002/0018210 A1 | 2/2002 | Maris |
| 2002/0039436 A1 | 4/2002 | Alumot et al. |
| 2002/0054704 A1 | 5/2002 | Smilansky et al. |
| 2002/0067478 A1 | 6/2002 | Karpol et al. |
| 2003/0133604 A1 | 7/2003 | Neumann |
| 2003/0197858 A1 | 10/2003 | Karpol et al. |

OTHER PUBLICATIONS

Wang, et al. (1995) "Picosecond Laser Pulse Generation in Monolithic Self–Q–Switched Solid–State Laser," *Optics Communications,* 114:439–41.

Billat et al., "Defect Partitioning: A New Methodology", SPIE, vol. 1087, Integrated Circuit Metrology, Inspection, and Process Control III, 1989, 207–215.

Batchelder et al., "Interferometric detection of forward scattered light from small particles", Applied Physics Letter, vol. 55(3), American Institute of Physics, Jul. 17, 1989, 215–217.

Teutsch et al., "Combining Electrical Defect Monitors with Automatic Visual Inspection Systems", SPIE, vol. 1087, Integrated Circuit Metrology and Process Control III, 1989, 189–199.

Darboux et al., "An Automated System for Submicrometer Defect Detection on Patterned Wafers", SPIE, vol. 1138, Optical Microlithography and Metrology for Microcircuit Fabrication, 1989, 172–177.

Comline News Service, Toray to Market, IC Inspection Equipment, Nov. 16, 1989, Tokyo, Japan.

Dataquest Incorporated Jul., SEMS Newsletter, "CD and Wafer Inspection Equipment: 1988 was a Very Good Year", 1989, 1–9.

Equipment Frontiers, "Holographic Wafer Inspection System", Solid State Technology, May 1987, 85–86.

Maldari, Francis S., "Capabilities of the Inspex EX2000 Patterned Wafer Inspection System", SPIE, vol. 774, Lasers in Microlithography, 1987, 1–7.

Pecen et al., "Counting Errors in Particulate Detection on Unpatterned Wafers", Solid State Technology, May 1987, 149–154.

Batchelder et al., "Applications of Particulate Inspection of Wafers in Semiconductor Manufacturing", Proceedings—Institute of Environmental Sciences, 1988, 4 pages.

Burggraaf, Pieter, "Auto Wafer Inspection: Tools for your Process Problems", Semiconductor International, Dec. 1988, 54–61.

Dom et al., "The F300: A System for Automatic Patterned Wafer Inspection", Machine Vision and Applications, vol. 1, 1998, 205–221.

Knox et al., "Inspecting IC Masks with a Differential Laser Scanning Inspection System", Solid State Technology, May 1977, 48–51.

Goodman et al., "Statistics of modal noise in fibers: a case of constrained speckle", Optical Society of America, vol. 6(7), Jul. 1981, 324–326.

O'Donnell, K.A., "Speckle statistics of doubly scattered light", Optical Society of America, vol. 72(11), Nov. 1982, 1459–1463.

Nicholas George, "About Speckle,", SPIE, vol. 556, International Conference on Speckle, 1985, 8–27.

Nakagawa et al., "Automatic Visual Inspection Using Digital Image Processing", Hitachi Review, vol. 34(1), 1985, 54–61.

Equipment Frontiers, "Automated Defect Detection System", Solid State Technology, Aug. 1985, 89–90.

Ehm et al., "Fully–automated Optical Inspection for VLSI Production", Elsevier Science Publishers B V (North–Holland), Microelectronic Engineering, vol. 5, 1986, 555–562.

Zollinger et al., "Impact of 1X Reticle Detects for Submicron Production Lithography", SPIE, vol. 633, Optical Microlithography V, 1986, 122–128.

Martin et al., "Limits of laser scattering defect inspection tools on patterned wafers", Proc. SPIE, vol. 2196, May 1994, 200–210.

Simpson, Robert, "Machine Vision in Semiconductor Wafer Inspection", Lasers & Optronics, 2 pages, 1996.

Kohler et al., "Speckle Reduction in Pulsed–Laser Photographs", Optics Communications, vol. 12(1), Sep. 1974, 24–28.

Bruning et al., "An Automated Mask Inspection System—AMIS", IEEE Trans. on Electron Devices, 1975.

Miller et al., "Second–order statistics of laser–speckle patterns", Journal of the Optical Society of America, vol. 65(7), Jul. 1975, 779–785.

Goodman, J.W., "Some fundamental properties of speckle", Journal of Optical Society of America, vol. 66(11) Nov. 1976, 1145–1150.

Veligdan et al., "Polyplanar Optic Display for Cockpit Application", SPIE, vol. 3363, Apr. 1998, 327–336.

Dingel et al., "Laser–diode microscope with fiber illumination", Optics Communications, vol. 93, 1992, 27–32.

Batchelder, J. Samuel, "Review of Contamination Detection on Patterned Surfaces", SPIE, vol. 774, Lasers in Microlithography, 1987, 8–12.

Funsten et al., "In–Line Defect Detection Metrology Tool Matching", IEEE, 1997, B–59–B–62, California.

Chen et al., "Machine vision algorithms for semiconductor wafer inspection: a project with Inspex", SPIE, vol. 3521, Nov. 1998, 221–228.

Browning et al., "Recent advances in automated patterned wafer inspection", SPIE, vol. 1087, Integrated Circuit Metrology, Inspection, and Process Control III, 1989, 440–445.

Armenakis, "Mapping Potential of the IRS–IC Pan Satellite Imagery", IAPRS, vol. 32, Part 4, 1998, 23–26, Germany.

Dataquest Incorporated, "New Products, New Entity in CD/WAFER Inspection", SEMMS Newsletters, Oct. 1990, 1–3.

Dataquest Incorporated, "Optical CD and Wafer Inspection Equipment Market Update", SEMS Newsletters, Oct. 1990, 1–5.

Surfscan 7000, Patterned Wafer Contamination Analyzer, Tencor Instruments, 1990, 9 pages, California.

Carpentier, David, "Defect Monitor and Charachterization Standard", IBM, Burlington Technical Bulletin, Sep. 1990, 1–12.

Coates et al., "Ultraviolet–Visible Microspectrophotometer System for Small–Spot Measurement and Characterization of Thin Films", SPIE—The International Society for Optical Engineering, vol. 1261, 1990, 3 pages.

Saloma et al., "Laser–diode microscope that generates weakly speckled images", Optical Society of America, Optics Letters, vol. 15:4, Feb. 15, 1990, 203–205.

Partio et al., "Reducing coherence in a fifth–harmonic YAG source (213 nm) for use in microlithography", J. Vac. Science Technology. B, vol. 9:6, Nov./Dec. 1991, 3126–3131.

Ranchin et al., "Speckle Reduction in Synthetic Aperture Radar Imagery using Wavelets", SPIE, vol. 2034, Mathematic Imaging, 1993, 432–441.

Holcman et al., "The use of PDI technology in the Orbot Wafer Inspection System", SMICON/Korea, Technical Symposium, Nov. 1993, 1–9.

Alumot et al., "Dual sensor technology for high–speed detection of 0.1 micron defects", SPIE, vol. 1926, Integrated Circuit Metrology, Inspection and Process Control VII, 1993, 1–12.

Freischald et al., "Speckle reduction by virtual spatial coherence", SPIE, vol. 1755, Interferometry: Techniques and Analysis, 1992, 38–43.

Ohmi, Tadahiro, "Ultraclean Technology: Innovation for Semiconductor Manufacturing", Solid State Technology, Oct. 1989, 51–56.

Okamoto et al., "Wafer Inspection Technology for Submicron Devices", SPIE, vol. 1087, Integrated Circuit Metrology, Inspection and Process Control III, 1989, 524–531.

Pope, Gregory, "Machine Vision Focuses on Profits", High Technology Business, Jan. 1989, 14–17.

Toro–Lira, Guillermo L., "Techniques for high speed SEM wafer inspection for production applications", SPIE, vol. 1087, Integrated Circuit Metrology, Inspection and Process Control III, 1989, 17–29.

Amako et al., "Speckle–noise reduction on kinoform reconstruction using a phase–only spatial light modulator", Applied Optics, vol. 34:17, Jun. 10, 1995, 3165–3171.

Eichhorn, et al., "Suppression of the speckle noise in solid polymer samples: a light scattering study", Optical Engineering, vol. 33:10, Oct. 1994, 3368–3371.

Sherman et al., "An Automated Defect Classification System for Semiconductor Wafers", SPIE, vol. 1907, Machine Vision Applications in Industrial Inspection, 1993, 1–8.

Simard et al., "Time–averaged speckle reduction in scanning active imaging systems", Optical Engineering, vol. 33:4, Apr. 1994, 1280–1286.

Author: Disclosed Anonymously, "Speckle reduction by fiber optic beam retardation", Research Disclosure Journal, Aug. 1987, 3 pages.

Wang et al., "Speckle reduction in laser projection systems by diffractive optical elements", Applied Optics, vol. 37:10, Apr. 1998, 1770–1775.

Ruiz et al., "Evaluation of a scale–space filter for speckle noise reduction in electronic speckle pattern interferometry", Optical Engineering, vol. 37:8, Aug. 1998, 2395–2401.

Brinkmann et al., "Interferometric testing of plane and cylindrical workpieces with computer–generated holograms", Optical Engineering, vol. 37:9, Sep. 1998, 2506–2511.

Kress, Stephen, "Machine vision changes wafer–testing ground rules", Machine Design, Oct. 9, 1997, 4 pages.

Harthong et al., "Speckle phase averaging in high–resolution color holography", Optical Society of America, vol. 14:2, Feb. 1997, 405–410.

Baliga, John, Editor, "Defect Detection on Patterned Wafers", Semiconductor International, May 1997, 64–70.

Lebart et al., "Speckle Filtering by Wavelet Analysis and Synthesis", SPIE, vol. 2825, Jul. 8, 1996, 8 pages.

Iwai et al., "Speckle Reduction in Coherent Information Processing", Proceedings of the IEEE, vol. 84:5, May 1996, 765–781.

Blacknell et al., "Speckle Reduction of SAR Images Using Neural Networks", SPIE, vol. 2584, 1995, 179–187.

US 6,924,891 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 10, 19, 20, 21 and 22 are determined to be patentable as amended.

Claims 2-9, 11-17 and 18, dependent on an amended claim, are determined to be patentable.

New claims 23-96 are added and determined to be patentable.

1. In the inspection of a patterned article used in the manufacture of semiconductor devices, a method of reducing speckle, said method comprising:
   effecting relative movement between an illuminating beam and said patterned article, said illuminating beam being obtained by modifying a coherent light beam so as to break, at least partially, its coherence;
   said modifying of said coherent light beam comprising:
   disposing a plurality of optical fiber bundles sequentially along a light path between a source of said illuminating beam and the patterned article, each of said plurality of fiber bundles having a predetermined number of fibers, each of said fibers having an input and an output, wherein fibers of a first bundle of said plurality of bundles receive said coherent light beam through said input and fibers of a last bundle of said plurality of bundles transmit an output beam through said output;
   *further comprising imaging the output of each of the fibers in said first bundle into the input of each of the fibers in a second bundle of said plurality of bundles.*

10. An inspection device, comprising: a source of a coherent light beam; and an optical apparatus, the apparatus comprising a plurality of optical fiber bundles positioned sequentially along a light path between the source and a patterned article to be inspected so as to break, at least partly, a coherence of said coherent light beam, each of said plurality of fiber bundles comprising a predetermined number of fibers, each of said fibers having an input and an output, wherein fibers of a first bundle of said plurality of bundles receive said light beam through said input and fibers of a last bundle of said plurality of bundles transmit an output beam through said output, *wherein the output of each of the fibers in said first bundle is imaged into the input of each of the fibers in a second bundle of said plurality of bundles.*

19. A method for electro-optically inspecting a patterned semiconductor wafer of dies for a defect, the method comprising:
   providing a repetitively pulsed laser illuminating source which produces a coherent laser beam;
   breaking at least partially a coherence of said coherent laser beam to produce an output light beam;
   illuminating at least one field of view in each of a plurality of wafer dies using said output light beam; and
   detecting a wafer defect using a die-to-die comparison method,
   wherein the breaking at least partially a coherence of said coherent laser beam comprises disposing a plurality of optical fiber bundles sequentially along a light path between a source of said illuminating beam and the patterned semiconductor wafer, each of said plurality of fiber bundles having a predetermined number of fibers, each of said fibers having an input and an output, wherein fibers of a first bundle of said plurality of bundles receive said coherent light beam through said input and fibers of a last bundle of said plurality of bundles transmit an output beam through said output,
   *further comprising imaging the output of each of the fibers in said first bundle into the input of each of the fibers in a second bundle of said plurality of bundles.*

20. A system for electro-optically inspecting a patterned semiconductor wafer of dies for a defect comprising:
   a repetitively pulsed laser illuminating source, providing a coherent laser beam for illuminating at least one field of view in each of a plurality of wafer dies;
   optical apparatus for breaking at least partially a coherence of said coherent laser beam to produce an output light beam; and
   a wafer defect detector, detecting a wafer using a die-to-die comparison method,
   wherein the optical apparatus for breaking at least partially a coherence of said coherent laser beam comprises a plurality of optical fiber bundles positioned sequentially along a light path of the coherent laser beam between the repetitively pulsed laser illuminating source and the patterned semiconductor wafer, each of said plurality of fiber bundles comprising a predetermined number of fibers, each of said fibers having an input and an output, wherein fibers of a first bundle of said plurality of bundles receive said light beam through said input and fibers of a last bundle of said plurality of bundles transmit an output beam through said output, *wherein the output of each of the fibers in said first bundle is imaged into the input of each of the fibers in a second bundle of said plurality of bundles.*

21. An electro-optical device for inspecting a patterned semiconductor wafer containing dies for a defect comprising:
   a repetitively pulsed laser illuminating source, providing a coherent laser beam for illuminating at least one field of view in each of a plurality of dies;
   optical apparatus for breaking at least partially a coherence of said coherent laser beam to produce an output light beam; and
   an imaging assembly including at least one detector ensemble including at least one two-dimensional matrix photo-detector,
   wherein the optical apparatus of breaking at least partially a coherence of said coherent laser beam comprises: a plurality of optical fiber bundles positioned sequentially along a light path of the coherent laser beam between the repetitively pulsed laser illuminating source and the patterned semiconductor wafer, each of said plurality of fiber bundles comprising a predetermined number of fibers, each of said fibers having an input and an output, wherein fibers of a first bundle of said plurality of bundles receiving said light beam through said input and fibers of a last bundle of said plurality of bundles transmitting an output beam through said output, *wherein the output of each of the fibers in said first bundle is imaged into the input of each of the fibers in a second bundle of said plurality of bundles.*

22. A method for electro-optically inspecting a patterned semiconductor wafer containing dies for a defect, comprising:

provoding an imaging assembly including at least one detector ensemble including at least one two-dimensional matrix photo-detector;

providing a reptitively pulsed laser illuminating source which produces a coherent laser beam; and breaking at least partially a coherence of said coherent laser beam to produce an output light beam, wherein the breaking at least partially a coherence of said coherent laser beam comprises disposing a plurality of optical fiber bundles sequentially along a light path between a source of said illuminating beam and the patterned semiconductor wafer, each of said plurality of fiber bundles having a predetermined number of fibers, each of said fibers having an input and an output, wherein fibers of a first bundle of said plurality of bundles receiving said coherent light beam through said input and fibers of a last bundle of said plurality of bundles transmitting an output beam through said output;

*further comprising imaging the output of each of the fibers in said first bundle into the input of each of the fibers in a second bundle of said plurality of bundles.*

23. *A method as claimed in claim 3, wherein there is an imaging lens disposed in between the first optical fiber bundle and the second optical fiber bundles and the imaging lens is arranged to image the output of each fiber in the first optical fiber bundle into the input of all fibers of the second optical fiber bundle.*

24. *A method as claimed in claim 3, wherein fibers in the first fiber bundle have different lengths and fibers in the second fiber bundle have different lengths.*

25. *A method as claimed in claim 24, wherein fibers of different lengths are randomly disposed within each bundle.*

26. *A method as claimed in claim 1, further comprising homogenizing, by a light scattering element, angles at which one or more intermediate beams exiting outputs of the fibers of the first bundle are received at inputs of fibers of a last bundle of said plurality of bundles.*

27. *A method as claimed in claim 1, wherein fibers in a fiber bundle have different lengths, and wherein a difference in length between every pair of fibers in the fiber bundle is greater than a coherence length of the coherent light beam.*

28. *A method as claimed in claim 1, further comprising disposing an imaging lens between fiber bundles in the plurality of fiber bundles so as to image the output of each fiber in one of the fiber bundles into the inputs of all fibers of another of the fiber bundles.*

29. *A method as claimed in claim 28, wherein fibers in a fiber bundle have different lengths, and wherein a difference in length between every pair of fibers in the fiber bundle is greater than a coherence length of the coherent light beam.*

30. *A method as claimed in claim 1, wherein fibers in the first fiber bundle have different lengths and fibers in the second fiber bundle have different lengths.*

31. *A method as claimed in claim 30, wherein fibers of different lengths are randomly disposed within each bundle.*

32. *A device as claimed in claim 12, wherein there is an imaging lens disposed in between the first optical fiber bundle and the second optical fiber bundles and the imaging lens is arranged to image the output of each fiber in the first optical fiber bundle into the input of all fibers of the second optical fiber bundle.*

33. *A device as claimed in claim 12, wherein fibers in the first fiber bundle have different lengths and fibers in the second fiber bundle have different lengths.*

34. *A device as claimed in claim 33, wherein fibers of different lengths are randomly disposed within each bundle.*

35. *A device as claimed in claim 10, further comprising a light scattering element, the light scattering element configured to receive one or more intermediate light beams exiting outputs of the fibers of the first bundle and homogenize angles at which the one or more intermediate light beams are received at inputs of fibers of the last bundle.*

36. *A device as claimed in claim 10, wherein fibers in a fiber bundle have different lengths, and wherein a difference in length between every pair of fibers in the fiber bundle is greater than a coherence length of the coherent light beam.*

37. *A device as claimed in claim 10, wherein the optical apparatus further comprises an imaging lens disposed between fiber bundles in the plurality of fiber bundles and arranged to image the output of each fiber in one of the fiber bundles into the imputs of all fibers of another of the fiber bundles.*

38. *A device as claimed in claim 37, wherein fibers in a fiber bundle have different lengths, and wherein a difference in length between every pair of fibers in the fiber bundle is greater than a coherence length of the coherent light beam.*

39. *A device as claimed in claim 10, wherein fibers in the first fiber bundle have different lengths and fibers in the second fiber bundle have different lengths.*

40. *A device as claimed in claim 39, wherein fibers of different lengths are randomly disposed within each bundle.*

41. *A method as claimed in claim 19, wherein there are first and second optical fiber bundles, said second optical fiber bundle being said last bundle, the method further comprising providing an output of each of the fibers in said first optical fiber bundle to an input of each of the fibers in said second optical fiber bundle.*

42. *A method as claimed in claim 41, wherein said predetermined number of fibers is different for each of said first and second optical fiber bundles.*

43. *A method as claimed in claim 41, wherein said predetermined number of fibers is the same for each of said first and second optical fiber bundles.*

44. *A method as claimed in claim 41, wherein at least some of the fibers in said first and second optical fiber bundles have different lengths.*

45. *A method as claimed in claim 44, wherein input ends of the fibers in at least one of said first and second optical fiber bundles are aligned.*

46. *A method as claimed in claim 44, wherein output ends of the fibers in at least one of said first and second optical fiber bundles are aligned.*

47. *A method as claimed in claim 41, wherein characteristics of at least some of the fibers in said first and second optical fiber bundles are selected from the group consisting of nonlinearity, difference in refractive indices, and difference in cladding.*

48. *A method as claimed in claim 41, wherein there is an imaging lens disposed in between the first optical fiber bundle and the second optical fiber bundles and the imaging lens is arranged to image the output of each fiber in the first optical fiber bundle into the input of all fibers of the second optical fiber bundle.*

49. *A method as claimed in claim 19, further comprising homogenizing, by a light scattering element, angles at which* one or more intermediate beams exiting outputs of the fibers of the first bundle are received at inputs of fibers of a last bundle of said plurality of bundles.

50. A method as claimed in claim 19, wherein fibers in a fiber bundle have different lengths, and wherein a difference in length between every pair of fibers in the fiber bundle is greater than a coherence length of the coherent light beam.

51. A method as claimed in claim 19, further comprising disposing an imaging lens between fiber bundles in the plurality of fiber bundles so as to image the output of each fiber in one of the fiber bundles into the inputs of all fibers of another of the fiber bundles.

52. A method as claimed in claim 51, wherein fibers in a fiber bundle have different lengths, and wherein a difference in length between every pair of fibers in the fiber bundle is greater than a coherence length of the coherent light beam.

53. A method as claimed in claim 19, wherein fibers in the first fiber bundle have different lengths and fibers in the second fiber bundle have different lengths.

54. A method as claimed in claim 53, wherein fibers of different lengths are randomly disposed within each bundle.

55. A system as claimed in claim 20, wherein there are first and second optical fiber bundles, said second optical fiber bundle being said last bundle, the method further comprising providing an output of each of the fibers in said first optical fiber bundle to an input of each of the fibers in said second optical fiber bundle.

56. A system as claimed in claim 55, wherein said predetermined number of fibers is different for each of said first and second optical fiber bundles.

57. A system as claimed in claim 55, wherein said predetermined number of fibers is the same for each of said first and second optical fiber bundles.

58. A system as claimed in claim 55, wherein at least some of the fibers in said first and second optical fiber bundles have different lengths.

59. A system as claimed in claim 58, wherein input ends of the fibers in at least one of said first and second optical fiber bundles are aligned.

60. A system as claimed in claim 58, wherein output ends of the fibers in at least one of said first and second optical fiber bundles are aligned.

61. A system as claimed in claim 55, wherein characteristics of at least some of the fibers in said first and second optical fiber bundles are selected from the group consisting of nonlinearity, difference in refractive indices, and difference in cladding.

62. A system as claimed in claim 55, wherein there is an imaging lens disposed in between the first optical fiber bundle and the second optical fiber bundles and the imaging lens is arranged to image the output of each fiber in the first optical fiber bundle into the input of all fibers of the second optical fiber bundle.

63. A system as claimed in claim 20, further comprising a light scattering element, the light scattering element configured to receive one or more intermediate light beams exiting outputs of the fibers of the first bundle and homogenize angles at which the one or more intermediate light beams are received at inputs of fibers of the last bundle.

64. A system as claimed in claim 20, wherein fibers in a fiber bundle have different lengths, and wherein a difference in length between every pair of fibers in the fiber bundle is greater than a coherence length of the coherent light beam.

65. A system as claimed in claim 20, wherein the optical apparatus further comprises an imaging lens disposed between fiber bundles in the plurality of fiber bundles and arranged to image the output of each fiber in one of the fiber bundles into the inputs of all fibers of another of the fiber bundles.

66. A system as claimed in claim 65, wherein fibers in a fiber bundle have different lengths, and wherein a difference in length between every pair of fibers in the fiber bundle is greater than a coherence length of the coherent light beam.

67. A system as claimed in claim 20, wherein fibers in the first fiber bundle have different lengths and fibers in the second fiber bundle have different lengths.

68. A system as claimed in claim 67, wherein fibers of different lengths are randomly disposed within each bundle.

69. An electro-optical device as claimed in claim 21, wherein there are first and second optical fiber bundles, said second optical fiber bundle being said last bundle, the method further comprising providing an output of each of the fibers in said first optical fiber bundle to an input of each of the fibers in said second optical fiber bundle.

70. An electro-optical device as claimed in claim 69, wherein said predetermined number of fibers is different for each of said first and second optical fiber bundles.

71. An electro-optical device as claimed in claim 69, wherein said predetermined number of fibers is the same for each of said first and second optical fiber bundles.

72. An electro-optical device as claimed in claim 69, wherein at least some of the fibers in said first and second optical fiber bundles have different lengths.

73. An electro-optical device as claimed in claim 72, wherein input ends of the fibers in at least one of said first and second optical fiber bundles are aligned.

74. An electro-optical device as claimed in claim 72, wherein output ends of the fibers in at least one of said first and second optical fiber bundles are aligned.

75. An electro-optical device as claimed in claim 69, wherein characteristics of at least some of the fibers in said first and second optical fiber bundles are selected from the group consisting of nonlinearity, difference in refractive indices, and difference in cladding.

76. An electro-optical device as claimed in claim 69, wherein there is an imaging lens disposed in between the first optical fiber bundle and the second optical fiber bundles and the imaging lens is arranged to image the output of each fiber in the first optical fiber bundle into the input of all fibers of the second optical fiber bundle.

77. An electro-optical device as claimed in claim 21, further comprising a light scattering element, the light scattering element configured to receive the one or more intermediate light beams exiting outputs of the fibers of the first bundle and homogenize angles at which the one or more intermediate light beams are received at inputs of fibers of the last bundle.

78. An electro-optical device as claimed in claim 21, wherein fibers in a fiber bundle have different lengths, and wherein a difference in length between every pair of fibers in the fiber bundle is greater than a coherence length of the coherent light beams.

79. An electro-optical device as claimed in claim 21, further comprising disposing an imaging lens between fiber bundles in the plurality of fiber bundles so as to image the output of each fiber in one of the fiber bundles into the inputs of all fibers of another of the fiber bundles.

80. An electro-optical device as claimed in claim 79, wherein fibers in a fiber bundle have different lengths, and wherein a difference in length between every pair of fibers in the fiber bundle is greater than a coherence length of the coherent light beam.

81. An electro-optical device as claimed in claim 21, wherein fibers in the first fiber bundle have different lengths and fibers in the second fiber bundle have different lengths.

82. An electro-optical device as claimed in claim 81, wherein fibers of different lengths are randomly disposed within each bundle.

83. A method as claimed in claim 22, wherein there are first and second optical fiber bundles, said second optical fiber bundle being said last bundle, the method further comprising providing an output of each of the fibers in said first optical fiber bundle to an input of each of the fibers in said second optical fiber bundle.

84. A method as claimed in claim 83, wherein said predetermined number of fibers is different for each of said first and second optical fiber bundles.

85. A method as claimed in claim 83, wherein said predetermined number of fibers is the same for each of said first and second optical fiber bundles.

86. A method as claimed in claim 83, wherein at least some of the fibers in said first and second optical fiber bundles have different lengths.

87. A method as claimed in claim 86, wherein input ends of the fibers in at least one of said first and second optical fiber bundles are aligned.

88. A method as claimed in claim 86, wherein output ends of the fibers in at least one of said first and second optical fiber bundles are aligned.

89. A method as claimed in claim 83, wherein characteristics of at least some of the fibers in said first and second optical fiber bundles are selected from the group consisting of nonlinearity, difference in refractive indices, and difference in cladding.

90. A method as claimed in claim 83, wherein there is an imaging lens disposed in between the first optical fiber bundle and the second optical fiber bundles and the imaging lens is arranged to image the output of each fiber in the first optical fiber bundle into the input of all fibers of the second optical fiber bundle.

91. A method as claimed in claim 22, further comprising homogenizing, by a light scattering element, angles at which one or more intermediate beams exiting outputs of the fibers of the first bundle are received at inputs of fibers of a last bundle of said plurality of bundles.

92. A method as claimed in claim 22, wherein fibers in a fiber bundle have different lengths, and wherein a difference in length between every pair of fibers in the fiber bundle is greater than a coherence length of the coherent light beam.

93. A method as claimed in claim 22, further comprising disposing an imaging lens between fiber bundles in the plurality of fiber bundles so as to image the output of each fiber in one of the fiber bundles into the inputs of all fibers of another of the fiber bundles.

94. A method as claimed in claim 93, wherein fibers in a fiber bundle have different lengths, and wherein a difference in length between every pair of fibers in the fiber bundle is greater than a coherence length of the coherent light beam.

95. A method as claimed in claim 22, wherein fibers in the first fiber bundle have different lengths and fibers in the second fiber bundle have different lengths.

96. A method as claimed in claim 95, wherein fibers of different lengths are randomly disposed within each bundle.

\* \* \* \* \*